(12) United States Patent
Takeuchi et al.

(10) Patent No.: US 11,527,325 B2
(45) Date of Patent: Dec. 13, 2022

(54) ANALYSIS APPARATUS AND ANALYSIS METHOD

(71) Applicant: Hitachi, Ltd., Tokyo (JP)

(72) Inventors: Wataru Takeuchi, Tokyo (JP); Takuma Shibahara, Tokyo (JP); Ken Naono, Tokyo (JP); Shinji Tarumi, Tokyo (JP); Shuntaro Yui, Tokyo (JP)

(73) Assignee: Hitachi, Ltd., Tokyo (JP)

(*) Notice: Subject to any disclaimer, the term of this patent is extended or adjusted under 35 U.S.C. 154(b) by 174 days.

(21) Appl. No.: 16/245,096

(22) Filed: Jan. 10, 2019

(65) Prior Publication Data

US 2019/0221311 A1    Jul. 18, 2019

(30) Foreign Application Priority Data

Jan. 18, 2018 (JP) .............................. JP2018-006370

(51) Int. Cl.
*G16H 50/20* (2018.01)
*G06N 3/02* (2006.01)
(Continued)

(52) U.S. Cl.
CPC .............. *G16H 50/20* (2018.01); *G06N 3/02* (2013.01); *G16H 50/50* (2018.01); *G16H 50/70* (2018.01)

(58) Field of Classification Search
CPC ........ G16H 50/20; G16H 50/50; G16H 50/70; G06N 3/02
(Continued)

(56) References Cited

U.S. PATENT DOCUMENTS 8,744,870 B2    6/2014  Shastri et al.
10,483,003 B1*  11/2019 McNair ................. G16H 10/60
(Continued)

FOREIGN PATENT DOCUMENTS

JP    2008-047154 A    2/2008
JP    2008-514334 A    5/2008
(Continued)

OTHER PUBLICATIONS

J. A. Wu, W. Hsu and A. A. T. Bui, "An Approach for Incorporating Context in Building Probabilistic Predictive Models," 2012 IEEE Second International Conference on Healthcare Informatics, Imaging and Systems Biology, San Diego, CA, 2012, pp. 96-105, doi: 10.1109/HISB.2012.30. (Year: 2012).*
(Continued)

*Primary Examiner* — Robert W Morgan
*Assistant Examiner* — Bennett Stephen Erickson
(74) *Attorney, Agent, or Firm* — Procopio, Cory, Hargreaves & Savitch LLP

(57) ABSTRACT

An analysis apparatus comprises: a generation module configured to generate a second piece of input data having a weight for a first feature item of a patient based on: a first piece of input data relating to the first feature item; a second feature item relating to a transition to a prediction target in a clinical pathway relating to a process for diagnosis or treatment; and a clinical terminology indicating relevance between medical terms; a neural network configured to output, when being supplied with the first piece of input data and the second piece of input data generated, a prediction result for the prediction target in the clinical pathway and importance of the first feature item; an edit module configured to edit the clinical pathway based on the prediction result and the importance output from the neural network; and an output module configured to output an edit result.

9 Claims, 14 Drawing Sheets

(51) Int. Cl.
*G16H 50/50* (2018.01)
*G16H 50/70* (2018.01)

(58) Field of Classification Search
USPC .............................................................. 705/2
See application file for complete search history.

(56) References Cited

U.S. PATENT DOCUMENTS

| | | | | |
|---|---|---|---|---|
| 2006/0064415 | A1* | 3/2006 | Guyon | G16B 40/00 |
| 2008/0097965 | A1 | 4/2008 | Alsafadi | |
| 2010/0145720 | A1* | 6/2010 | Reiner | G16Z 99/00 |
| | | | | 705/2 |
| 2012/0310667 | A1 | 12/2012 | Altman et al. | |
| 2012/0310694 | A1 | 12/2012 | Van Zon et al. | |
| 2014/0095186 | A1* | 4/2014 | Gotz | G06Q 10/0637 |
| | | | | 705/2 |
| 2016/0063212 | A1* | 3/2016 | Monier | G16H 10/60 |
| | | | | 705/3 |
| 2016/0283686 | A1* | 9/2016 | Hu | G06N 20/00 |
| 2017/0083682 | A1* | 3/2017 | McNutt | A61N 5/1038 |
| 2017/0177822 | A1* | 6/2017 | Fogel | G16H 50/20 |
| 2018/0285731 | A1* | 10/2018 | Heifets | G06N 3/0454 |

FOREIGN PATENT DOCUMENTS

| | | |
|---|---|---|
| JP | 2012-243268 A | 12/2012 |
| JP | 2013-513847 A | 4/2013 |
| JP | 2013-175053 A | 9/2013 |
| JP | 2017-168129 A | 9/2017 |

OTHER PUBLICATIONS

Ribeiro, M. T. et al. ""Why Should I Trust You?" Explaining the Predictions of Any Classifier", KDD 2016, 10 pages, San Francisco, CA, USA, ACM, 2016.

Hastie, T. et al. "The Elements of Statistical Learning, Data Mining, Inference, and Prediction" Springer Series in Statistics, 2001, 764 pages, https://web.stanford.edu/~hastie/Papers/ESLII.pdf.

\* cited by examiner

| ITEM | VALUE | UNIT | IMPORTANCE |
|------|-------|---------|-----------|
| A | a | % | High |
| B | b | mmHg | Low |
| C | c | mmol/ml | Middle |
| D | d | YEN | None |
| E | e | mg | Very high |

Fig. 14

ANALYSIS APPARATUS AND ANALYSIS METHOD

CLAIM OF PRIORITY

The present application claims priority from Japanese patent application JP 2018-6370 filed on Jan. 18, 2018, the content of which is hereby incorporated by reference into this application.

BACKGROUND OF THE INVENTION

This invention relates to a computer architecture.

At a time of intervention in a patient in terms of diagnosis or treatment, a doctor determines intervention necessity or an intervention method based on the clinical guidelines or other such medical consensus information and the doctor's own experience. The clinical guidelines are high in evidence level, and are used as a basis for doctors conducting diagnosis or treatment. However, boundary conditions are often ambiguous for an actual operation based on the guidelines. Therefore, the actual operation based on the guidelines is highly dependent on the interpretation and decision of each individual doctor.

Meanwhile, there is a case in which such software as to support decision making based on machine learning or so-called artificial intelligence (AI) is used. In this case, a recommended intervention varies depending on features (for example, basic information including an age and a body weight and diagnosis-or-treatment information including an examination value and a contracted disease) of each patient recorded as data.

In JP 2008-47154 A, there is disclosed a clinical path operation support information system including: a clinical path analysis environment including a function of analyzing accumulated records on diagnosis and treatment to create, correct, and store a clinical path; and a function of selecting an optimal clinical path suitable for a condition of a patient from among accumulated clinical paths, in which the clinical path analysis environment includes a function of evaluating a process for diagnosis or treatment and a function of evaluating the clinical path.

In JP 2013-513847 A, there are disclosed a system and a method involving: loading and displaying a guideline graph based on first user input, receiving second user input for selecting a desired part of the guideline graph, and processing the second user input in order to load and display a subgraph including the desired part of the guideline graph.

In JP 2008-514334 A, there is disclosed a system for and a method of executing an executable clinical practical guideline for providing guidance in treating a patient. The system includes: a guideline repository configured to store a plurality of executable clinical practical guidelines; at least one interface configured to input clinical situation data associated with at least one of the patient or the treatment of the patient; and a display. When receiving the clinical situation data, a server of the system automatically selects an appropriate clinical practical guideline, and uses a visual navigator on the display to display the guideline. The server automatically provides the guideline at a current extraction level and provides the user with a visual navigator for defining the current extraction level. Meanwhile, when a signal generated by the user through manual selection via a UI is received, the guideline and the extraction level of the guideline are displayed. The extraction level can be changed by user input in both manual and automatic modes.

In U.S. Pat. No. 8,744,870 B2, there is disclosed a system for predicting one or a plurality of clinical pathways and resource requirements for at least one patient. This system includes an input module for receiving input relating to patient diagnosis data, and the patient diagnosis data includes information identified during the diagnosis of the patient. This system also includes a repository configured to store data including at least one of patient data or an existing clinical pathway. The patient data includes at least one piece of patient diagnosis data received from the input module, and includes patient history data including: past patient treatment data and patient demographic data including patient demographic details. This system also includes a clinical pathway prediction module for predicting a clinical pathway by applying a predetermined analysis model on patient data and existing clinical pathways. This system further includes a resource requirement prediction module for predicting the resource requirement for the patient.

In US 2012/0310667 A1, there is disclosed a clinical pathway system, which manages a process called "clinical pathway" for a medical professional to diagnose conditions and prescribe treatments or tests, and allows a physician or other healthcare professional to focus on decision making and patient care using clinical pathways programmed as spheres in a network connected by business rules.

In JP 2012-243268 A, there is disclosed a task flow retrieving apparatus, which is configured to: receive input of a task flow to be used as a search condition when retrieving a task flow from among task flows accumulated in an information processing apparatus; acquire task flows to be used as a search target from a storage module; calculate a similarity degree of the compared task flow with respect to the task flow set as the search condition based on a matching degree between combinations of each individual task and an actor for performing the individual task, which are included in the task flow set as the search condition and the task flows set as the search target; and present search results based on the individually calculated similarity degrees.

In JP 2013-175053 A, there is disclosed an XML document search apparatus, which is configured to: analyze a set of XML documents to be used as a search target; create a sequence group including a sequence for storing a shape of a DOM tree based on structure information on the XML documents and at least one sequence for recording a type of a structural path corresponding to each node of the DOM tree; and scan the sequence and the sequence group, to thereby calculate a part that matches the structural path serving as a search query.

In JP 2017-168129 A, there is disclosed an electronic medical record system, which is configured to: call a first data management process for a first data management operation, which defines a first set of compliance policies of a first healthcare participant for the first data management operation; and call a second data management process for the first data management operation, which defines a second set of compliance policies of a second healthcare participant for the first data management operation, which is different from the first set of compliance policies.

As a method of predicting output data from input data, there is a method using a so-called perceptron. The perceptron outputs a predicted value based on a calculation result of a linear combination of a feature vector used as input and a weight vector. A neural network, which is also known as multi-perceptron, is a technology having an ability to solve a linearly inseparable problem by overlaying a plurality of perceptrons in multiple tiers, and emerged in the 1980s.

Since about 2012, a neural network that introduces dropout or other such new technology is called "deep learning".

In a machine learning field, the term "learning" refers to calculating a learning parameter (for example, weight vector in the perceptron) so as to minimize an error between a predicted value obtained from the feature vector and an actual value (true value). After a learning process is completed, a new predicted value can be calculated from data that has not been used for learning (hereinafter referred to as "test data"). In the perceptron, a magnitude of each element value of the weight vector is used as importance of a factor that has contributed to a prediction.

Meanwhile, in a neural network including deep learning, each element of the feature vector is subjected to a weighted product-sum operation with another element each time the each element passes through the perceptron, which makes it difficult to know the importance of each single element in principle.

In Ribeiro, Marco Tulio, Sameer Singh, and Carlos Guestrin, "Why should I trust you?: Explaining the predictions of any classifier.", Proceedings of the 22nd ACM SIGKDD International Conference on Knowledge Discovery and Data Mining, ACM, 2016 (hereinafter referred to as "Non-patent Literature 1"), there is described a method of newly learning a linear regression so as to be able to explain an identification result of deep learning or other such machine learning method that does not have a function of calculating importance of a feature. In addition, a logistic regression is a machine learning model equivalent to the perceptron, and is most widely used in all fields. For example, a logistic regression illustrated on page 119 of Friedman J, Trevor H, Robert T, "The elements of statistical learning", second edition, New York: Springer series in statistics, 2001, has a function of calculating the importance of the feature for all data samples.

However, the machine learning is generally a so-called "black box method". The method in Non-patent Literature 1 is merely attempting to provide an explanation with the linear regression in a retroactive manner, and there is no mathematical guarantee that the importance of the feature used for a prediction in deep learning can be completely calculated. In addition, when the linear regression can completely achieve the same prediction accuracy as that of the deep learning, the deep learning itself is no longer required in the first place, which raises a contradiction in constructive concept of the methods. The logistic regression also has no function of calculating the importance of the feature for each individual data sample.

Therefore, relevance between a prediction result of the machine learning model and selection criteria (clinical pathway) of diagnosis or treatment based on the clinical guidelines or other such medical evidence is unknown. As a result, it is difficult to interpret the prediction result and the selection criteria in association with each other. For example, a recommended intervention varies depending on features (for example, basic information including an age and a body weight and diagnosis-or-treatment information including an examination value and a contracted disease) of each patient recorded as data, but it is not easy to present, to a doctor, a basis on which to recommend the recommended intervention.

SUMMARY OF THE INVENTION

This invention has been made in view of the above-mentioned points, and therefore has an object to achieve improvement in interpretability of relevance between a feature that has contributed to a prediction based on machine learning and a clinical pathway.

An aspect of the invention disclosed in this application is an analysis apparatus, comprising: a generation module configured to generate a second piece of input data having a weight for a first feature item of a patient based on: a first piece of input data relating to the first feature item; a second feature item relating to a transition to a prediction target in a clinical pathway relating to a process for diagnosis or treatment; and a clinical terminology indicating relevance between medical terms; a neural network configured to output, when being supplied with the first piece of input data and the second piece of input data generated by the generation module, a prediction result for the prediction target in the clinical pathway and importance of the first feature item; an edit module configured to edit the clinical pathway based on the prediction result and the importance, which have been output from the neural network; and an output module configured to output an edit result obtained through the edit performed by the edit module.

According to the representative embodiments of this invention, it is possible to achieve improvement in interpretability of relevance between a feature that has contributed to a prediction based on machine learning and a clinical pathway. Other objects, configurations, and effects than those described above are clarified by the following description of an embodiment.

BRIEF DESCRIPTION OF THE DRAWINGS

FIG. 14 is an explanatory diagram for illustrating a screen example (Case 5) for displaying the explanation-provided clinical pathway.

DETAILED DESCRIPTION OF THE PREFERRED EMBODIMENTS

In an embodiment of this invention, when a prediction model for machine learning is used to output a prediction result thereof, an emphasized feature is visualized, to thereby improve interpretability of relevance between the feature that has contributed to a prediction and a clinical pathway, and facilitate introduction of a machine learning model into a task of diagnosis or treatment. In other words, it is possible to present information for convincing a doctor, which includes a reason and a basis for a highly accurate prediction result.

In addition, it requires much time to accumulate medical evidence including medical research papers, which requires much time to update information on a related-art clinical pathway. However, according to this embodiment, an explanation of the relevance with the prediction result output through use of the prediction model for the machine learning is easily provided, and hence it is possible to promote an increase in update speed due to the update of the information on the clinical pathway based on not only the related-art medical evidence but also on actual clinical data. Therefore, it is possible to improve the reliability of the clinical pathway.

The clinical pathway (also referred to as "clinical path") refers to the clinical guidelines or other such information relating to a process (also referred to as "selection criteria") of diagnosis or treatment, and includes, for example, an order of diagnosis and treatment and a progression order of a disease. The clinical path in this embodiment is set as computer readable information (for example, a flow chart, a table, and other such graphic data including character strings and text data representing at least one sentence).

<Example of Updating Clinical Pathway>

Figure 1:
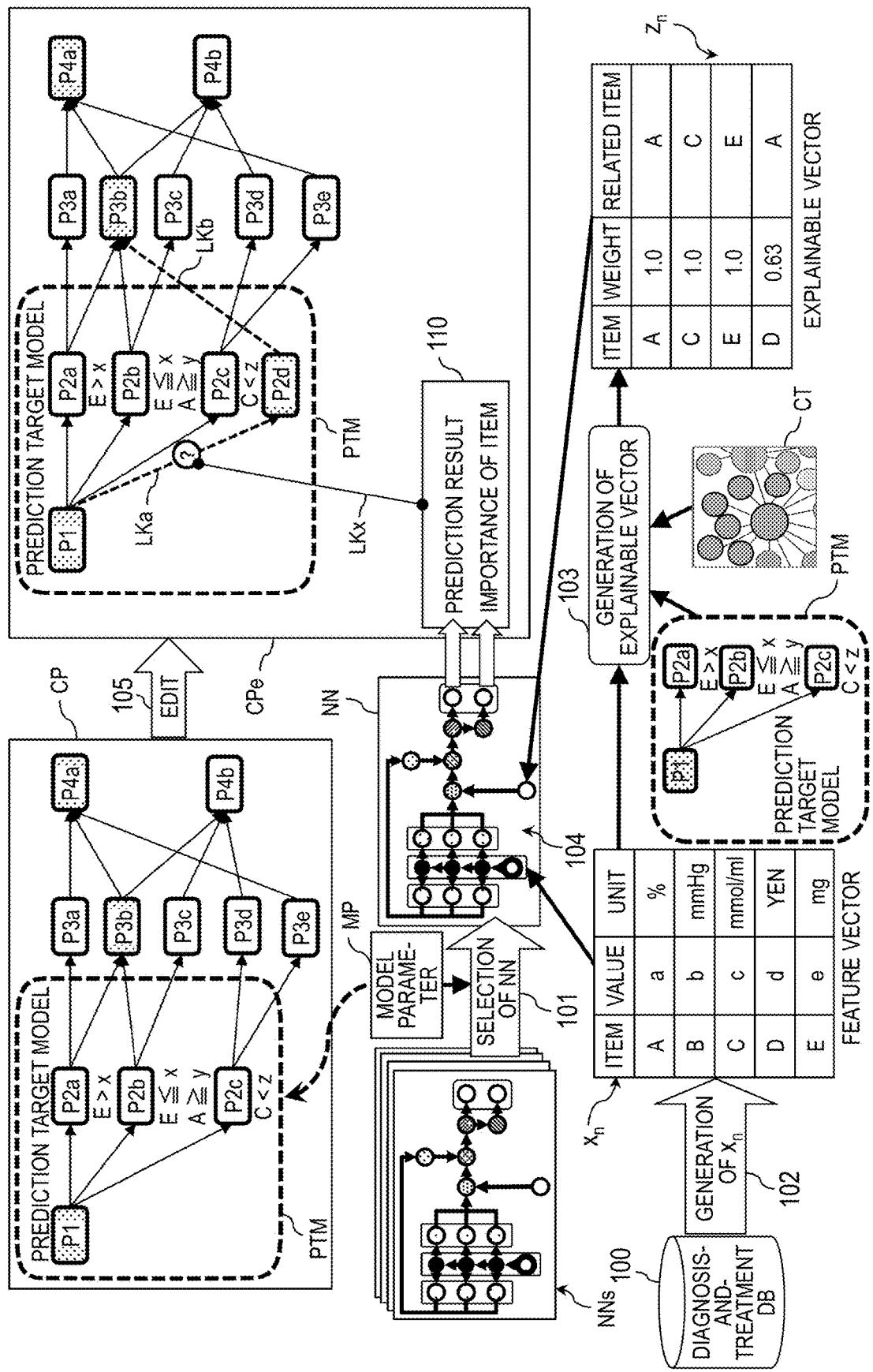
FIG. 1 is an explanatory diagram for illustrating an example of updating a clinical pathway.

FIG. 1 is an explanatory diagram for illustrating an example of updating a clinical pathway. The update of a clinical pathway CP is executed by selection 101 of a neural network NN, generation 102 of a feature vector $x_n$, generation 103 of an explainable vector $z_n$, prediction 104 based on the selected neural network NN, and edit 105 of the clinical pathway CP, to thereby generate and display an explanation-provided clinical pathway CPe. In this example, it is assumed to be predicted which one of nodes P2a, P2b, and P2c serving as prediction targets in a prediction target model PTM forms an optimal pathway as a diagnosis-and-treatment pathway extending from a node P1 serving as a prediction starting point of the clinical pathway CP and passing through a node P3b to reach a node P4a.

In the selection 101 of the neural network NN, with reference to a model parameter MP, the neural network NN appropriate for a prediction of the prediction target model PTM is selected from a neural network group NNs. In general, a neural network includes an input layer, an output layer, and at least one intermediate layer, which is located between the input layer and the output layer, and is configured to perform calculation by supplying data from the previous layer and a learning parameter to an activation function to output a result of the calculation to the subsequent layer.

A normal neural network outputs only the prediction result, but the neural network NN in this embodiment outputs not only the prediction result but also importance of a feature item (hereinafter referred to simply as "item"). It is assumed that, for example, each neural network NN in the neural network group NNs is included for each prediction target model PTM, and is supplied with training data through supervised learning, to thereby construct a learning model.

The model parameter MP is information including the prediction target model PTM and a prediction parameter. The prediction target model PTM refers to a diagnosis-and-treatment pathway extending from a node serving as a prediction starting point to a node serving as a prediction target. For example, in the prediction target model PTM illustrated in FIG. 1, a symptom P1 serves as the prediction starting point, and treatments P2a to P2d serve as the prediction targets. The prediction parameter is a parameter for setting, for example, edit information on deletion, selection, addition, or other such edit to be performed on a prediction target and a method of ranking prediction targets.

Specifically, for example, the prediction target model PTM is set as a diagnosis-and-treatment pathway indicating in the case of the symptom P1 that the treatment P2a is appropriate when an examination result of a relevant patient is E>x (mg), the treatment P2b is appropriate when E≤x (mg) and A≥y (%), and the treatment P2c is appropriate when C<z (mmol/ml). A node of a non-prediction target may be included in a pathway between the prediction starting point and the prediction target.

The above-mentioned criteria "E>x (mg)", "E≤x (mg) and A≥y (%)", and "C<z (mmol/ml)" are clinical pathway branch criteria. The clinical pathway branch criteria are, for example, branch criteria for a node on the diagnosis-and-treatment pathway. In addition, the clinical pathway branch criteria may include information (for example, an age and a gender) for designating personal information on a patient.

In addition, a prediction target that is not included in the prediction target model PTM can be added to the model parameter MP. For example, when the treatment P2d is not included in the prediction target model PTM of the clinical pathway CP, but there is a possibility that the treatment P2d becomes appropriate in the most recent research paper or actual clinical data, the treatment P2d can be included in the model parameter MP as an additional prediction target. In this manner, a delay of the update of the clinical pathway CP can also be handled.

In the generation 102 of the feature vector $x_n$, the feature vector $x_n$ indicating the feature of the patient is generated. The feature vector $x_n$ is a vector to be supplied to the selected neural network NN, and is generated from patient data extracted from a diagnosis-and-treatment DB 100. The diagnosis-and-treatment DB 100 refers to a database configured to store an electronic medical record for each patient. Therefore, the "item" serving as an element indicating a feature in the feature vector $x_n$ includes: the personal information including an age, a gender, and a blood type of a patient; a type of a disease or an external wound; a type of treatment, surgical operation, or examination; a dose of administered medication; a diagnostic image; and a cost. The "value" is a value indicating the "item". A "unit" is a reference for expressing the "value" by a numerical value.

For example, when the "item" is the "administered medication" with the dose being "0.879 (mg)", the "value" is "0.879", and the unit is "(mg)". When a feature vector is a one-dimensional column vector regarding the "value", the "item" and the "unit" are assumed to be determined based on a position of the "value".

In the generation 103 of the explainable vector $z_n$, the feature vector $x_n$, the prediction target model PTM, and a clinical terminology CT are used to generate an explainable vector $z_n$. The explainable vector $z_n$ refers to a vector for explaining importance of the item in the feature vector $x_n$, and is supplied to the neural network NN together with the feature vector $x_n$. The "weight" is a value indicating a degree of the relevance to a "related item". In this embodiment, the "weight" is a value ranging from "0" to "1". The higher value indicates the higher relevance. The "related item" refers to an item relating to the "item" in the clinical terminology CT.

The "related item" is obtained by referring to the clinical terminology CT in the generation 103 of the explainable vector $z_n$. The clinical terminology CT refers to information representing medical terms and relevance therebetween, and is, for example, network information using the medical terms as nodes and the relevance as a link. The link indicates relevance between medical terms located at both ends of the link. The relevance is expressed by, for example, a link length. The shorter link length indicates the higher relevance degree. As in cases of the items A, C, and E, when the "item" is included in the prediction target model PTM and matches the "related item", the weight takes a maximum value of "1". When the "item" is not included in the prediction target model PTM, the reciprocal of the link length to the "item" in the prediction target model PTM is set as the weight.

In the prediction 104 based on the selected neural network NN, the feature vector $x_n$, and the explainable vector $z_n$ are supplied to the selected neural network NN, to thereby calculate the prediction result and the importance of the item. The prediction result is, for example, a probability of becoming any one of the prediction targets P2a to P2c.

When the model parameter MP includes the additional prediction target P2d, a probability of becoming the prediction target P2d is also calculated as the prediction result. The importance of the item is the importance of each item in the feature vector $x_n$. In this example, the higher value indicates the higher importance. The importance of the item indicates in turn which item contributes to the prediction result having the highest probability.

In the edit 105 of the clinical pathway CP, the clinical pathway CP is edited through use of the prediction result and the importance of the item. For example, when the treatment P2d, which is a prediction target that is not included in the prediction target model PTM and has been added from the model parameter MP, has the highest probability, a link (transition) LKa coupling P1 to P2d and a link LKb coupling P2d to P3b are generated.

In addition, the link LKa and the explanation information 110 are associated with each other by a link LKx. The explanation information 110 is information including the prediction result and the importance of the item. In the case of this example, the explanation information 110 serves as a basis for a transition from a prediction starting point P1 to the additional prediction target P2d instead of the prediction targets P2a to P2c. This processing obtains the explanation-provided clinical pathway CPe having the clinical pathway CP associated with the explanation information 110. The explanation-provided clinical pathway CPe is displayed on, for example, a monitor.

In this manner, by visualizing the item having a high importance in the prediction model for the machine learning when outputting a prediction result thereof, it is possible to achieve improvement in interpretability of the relevance between the item that has contributed to the prediction and the clinical pathway CP, can facilitate introduction of the machine learning into a task of diagnosis or treatment. Therefore, it is possible to present information for convincing a doctor, which includes a reason and a basis for a highly accurate prediction result.

<Example of Rearranging Feature Vectors $x_n$>

The AI has an ability to solve a linearly inseparable problem, but it is unknown how the AI has reached such decision. In particular, deep learning or other such machine learning method has high prediction accuracy but low explanatory ability. For example, when the AI outputs a diagnosis result "having high tendency to catch a cold" for a certain patient, the doctor cannot explain why the AI has obtained such a result. When the AI can determine its cause as well, the doctor can conduct appropriate treatment for the patient.

Figure 2:
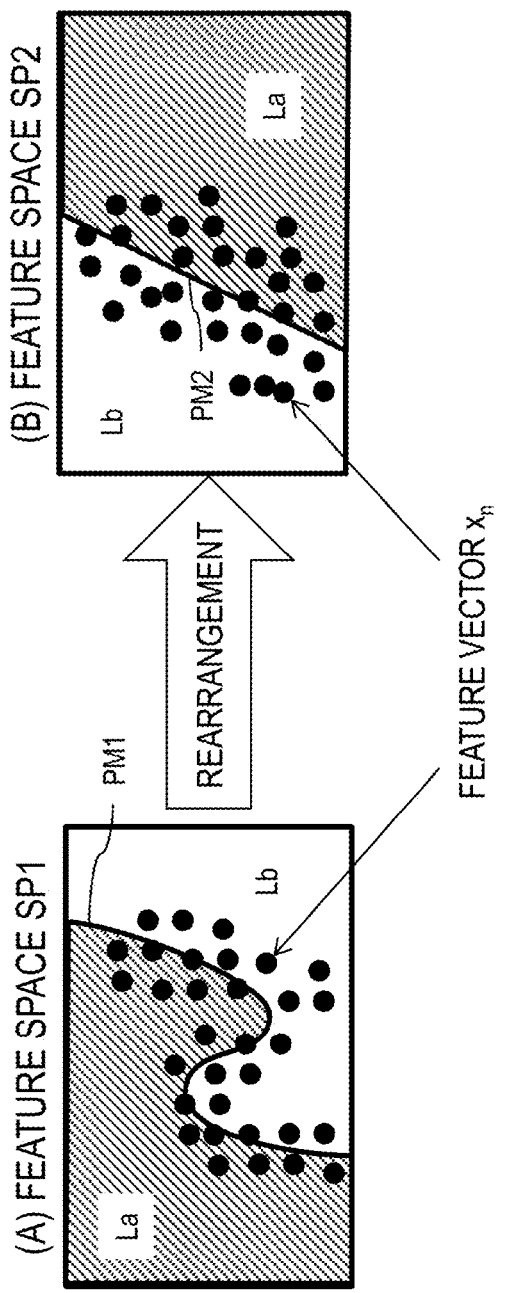
FIG. 2 is an explanatory diagram for illustrating an example of rearranging feature vectors.

FIG. 2 is an explanatory diagram for illustrating an example of rearranging feature vectors. In part (A), a feature space SP1 includes a plurality of feature vectors $x_n$ (n=1, 2, . . . , N, where N represents, for example, the number of patients). The plurality of feature vectors $x_n$ are identified into correct answer labels La and Lb by, for example, a non-linear prediction model PM1. In part (B), a feature space SP2 includes a plurality of feature vectors $x_n$. The plurality of feature vectors $x_n$ are identified into correct answer labels La and Lb by, for example, a linear prediction model PM2.

In part (A), deep learning or other such machine learning method newly learns a linear regression in order to explain the prediction model PM1 being an identification result. Specifically, for example, this machine learning method involves executing such retroactive processing to locally perform linear approximation after obtaining the prediction model PM1. However, in such retroactive processing, it is unknown whether or not a local part of the prediction model PM1 subjected to the linear approximation can correctly explain the feature vector $x_n$. Above all, in order to execute the linear approximation being a logistic regression, it is required to execute the machine learning two times in total.

The prediction model PM2 in part (B) is linear, and hence reference to an inclination thereof clarifies which parameter in the feature space SP2 is used to assign weights to the feature vector $x_n$, which allows the feature vector $x_n$ to be correctly explained. In this embodiment, without obtaining the non-linear prediction model PM1 for the plurality of feature vectors $x_n$ as in part (A), the plurality of feature vectors $x_n$ in the feature space SP1 are rearranged into another feature space SP2. The linear prediction model PM2 is thus obtained, and hence it is clarified which parameter in the feature space SP2 is used to assign weights to the feature vector $x_n$, which allows the feature vector $x_n$ to be correctly explained depending on their importance.

In other words, for each sample (for example, for each patient) having the feature vector $x_n$, the user is allowed to know which factor (feature) contained in the feature $x_n$ has contributed to the prediction result, and therefore easily explain how such a prediction result has been obtained. Therefore, it is possible to achieve improvement in the explanatory ability based on the machine learning. In the above-mentioned example, it is clarified why the AI has output the diagnosis result "the treatment P2d has been determined" for a certain patient (for example, the reason is that a value (examination result) of an item E is abnormally high). In addition, it is not required to execute the machine learning as often as two times unlike in part (A), and hence it is possible to achieve more efficient machine learning. Therefore, it is possible to quickly provide such an explanation as described above.

<Example of System Configuration>

Figure 3:
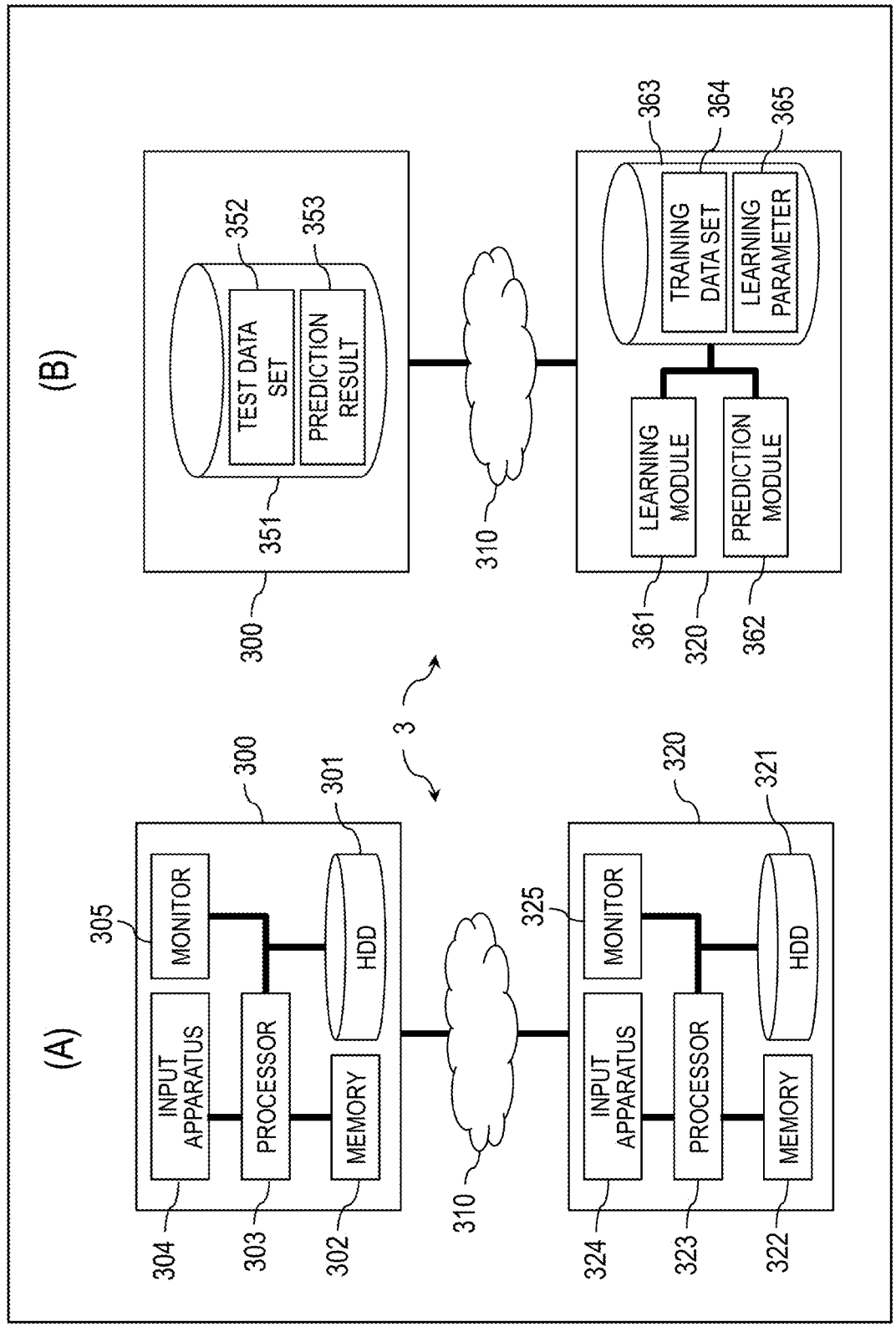
FIG. 3 is a block diagram illustrating an example of a configuration of an analysis system.

FIG. 3 is a block diagram illustrating an example of a configuration of an analysis system. While a server-client type analysis system 3 will be taken by way of example in FIG. 3, the data analysis system may be a stand-alone type. (A) is a block diagram illustrating an example of a hardware configuration of the analysis system 3, and (B) is a block diagram illustrating an example of a functional configuration of the analysis system 3. In (A) and (B), the same configuration is denoted by the same reference character.

The analysis system 3 is configured such that a client terminal 300 and an analysis apparatus 320 that is a server is communicably connected to each other by a network 310.

In (A), the client terminal 300 has an HDD (hard disk drive) 301 that is an auxiliary storage device, a memory 302 that is a main storage device, a processor 303, an input device 304 that is a keyboard and a mouse, and a monitor 305. The analysis apparatus 320 has an HDD 321 that is an auxiliary storage device, a memory 322 that is a main storage device, a processor 323, an input device 324 that is a keyboard and a mouse, and a monitor 325. It is noted that the main storage device, the auxiliary storage device, and a transportable storage medium, which is not shown, will be generically referred to as "memory devices." The memory devices each store the neural network NN and learning parameters of the neural network NN.

In (B), the client terminal 300 has a client database (DB) 351. The client DB 351 is stored in the memory device such as the HDD 301 or the memory 302. The client DB 351 stores a test data set 352 and a prediction result 353. The test data set 352 is a set of test data. The prediction result 353 is data obtained from a prediction module 362 via the network 310. It is noted that one or more client terminals 300 are present in the case of the server-client type.

The analysis apparatus 320 has a learning module 361, the prediction module 362, and a server database (DB) 363. The learning module 361 is a functional module configured to output the learning parameters 365 by executing such learning processing as to supply the feature vector $x_n$ to the neural network NN as the training data, compare the feature vector $x_n$ with a correct answer label $t_n$, and perform differential reverse propagation learning thereon.

The prediction module 362 is a functional section that constructs a first neural network 300 using the learning parameters 365, that executes a prediction process by applying the test data to the neural network NN, and that outputs the prediction result 353 to the client terminal 300. The learning module 361 and the prediction module 362 realize functions thereof by causing the processor 323 to execute a program stored in the memory device such as the HDD 321 and the memory 322.

The server DB 363 stores a training data set 364 and the learning parameters 365. The training data set 364 includes images $x_n$ that are an example of the feature vectors and correct labels $t_n$. The learning parameters 365 are output data from the learning module 361 and include matrices $W^l_D$, $W^l_R$, $W^l_H$, and $W_A$, and a weight vector $w_o$. It is noted that the neural network to which the learning parameters are set will be referred to as "prediction model."

It is noted that the analysis apparatuses 320 may be configured with a plurality of data analysis apparatuses. For example, a plurality of analysis apparatuses 320 may be present for load distribution. Furthermore, the analysis apparatus 320 may be configured with a plurality of parts according to functions. For example, the analysis apparatus 320 may be configured with a first server that includes the learning module 361 and the server DB 363 and a second server that includes the prediction module 362 and the server DB 363. Alternatively, the analysis apparatus 320 may be configured with a first analysis apparatus that includes the learning module 361 and the prediction module 362 and a second analysis apparatus that includes the server DB 363. In another alternative, the analysis apparatus 320 may be configured with a first server that includes the learning module 361, a second analysis apparatus that includes the prediction module 362, and a third analysis apparatus that includes the server DB 363.

<Example of Structure of Neural Network>

Figure 4:
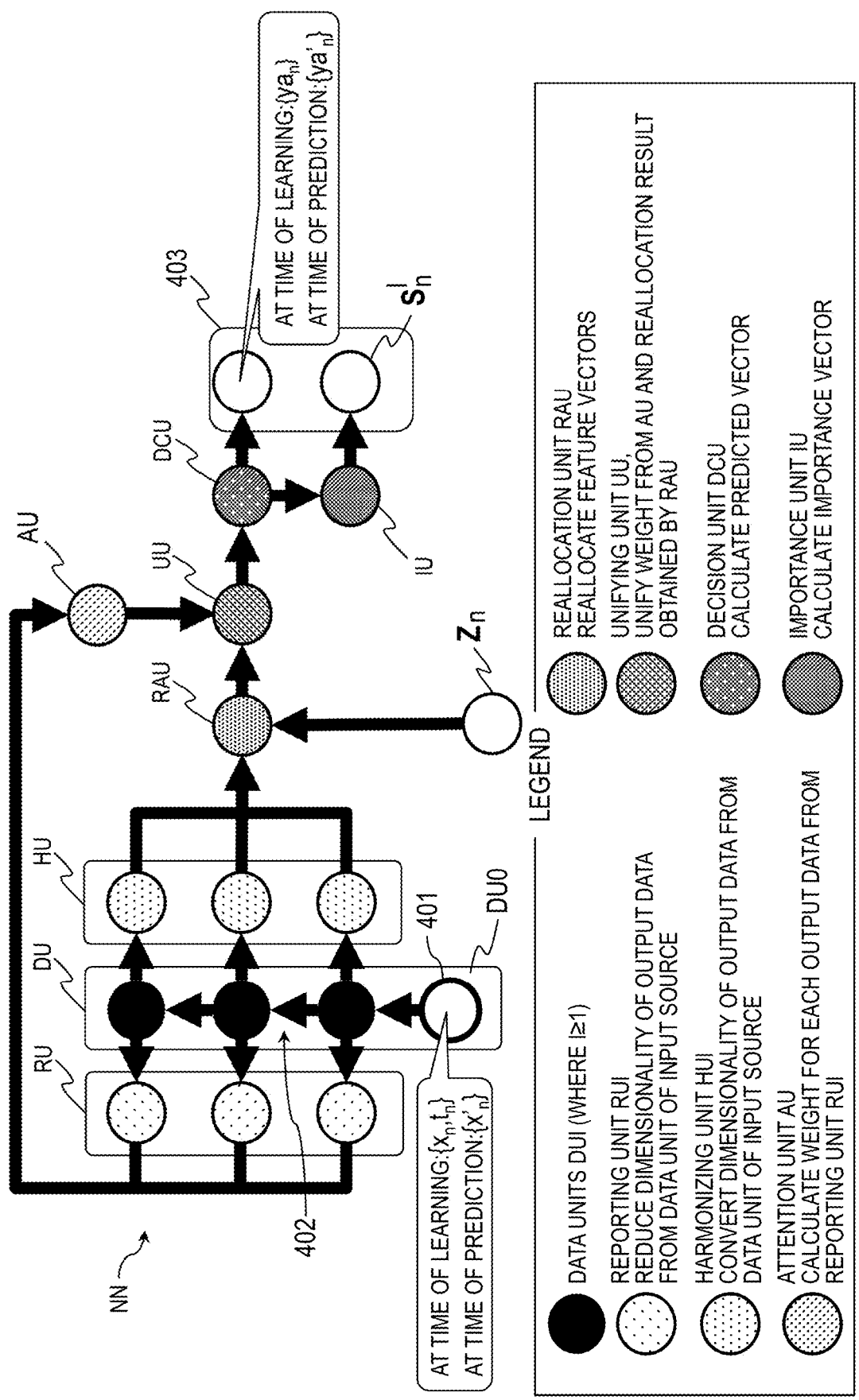
FIG. 4 is an explanatory diagram for illustrating an example of a structure of a neural network in this embodiment.

FIG. 4 is an explanatory diagram for illustrating an example of a structure of a neural network in this embodiment. The neural network NN includes a data unit group DU, a reporting unit group RU, a harmonizing unit group HU, an attention unit AU, a reallocation unit RAU, a unifying unit UU, a decision unit DCU, and an importance unit IU.

The data unit group DU is structured by coupling a plurality of data units DUl (l represents a hierarchical number, where $1 \leq l \leq L$ and L represents a hierarchical number of the lowermost tier, where L=4 in FIG. 4) in series. A data unit DU1 with l=1 indicating the uppermost tier corresponds to an input layer 401 of the neural network NN, and the data units DUl with $l \geq 2$ correspond to an intermediate layer 402 (also referred to as "hidden layer") of the neural network NN. The data unit DUl is a perceptron configured to receive input of output data from the data unit DU(l−1) in the previous stage and calculate output data through use of a learning parameter of the own data unit DUl to output the output data.

In this case, the data unit DU1 holds the training data at a time of learning performed by the learning module 361. In this case, the training data is, for example, sample data formed of combinations $\{x_n$ and $t_n\}$ of the feature vector $x_n$ and the correct answer label $t_n$ being its true value (n=1, 2, . . . , N, where N represents, for example, the number of patients). The feature vector $x_n$ is handled as a d-dimensional vector when the number of items is set to d (integer that satisfies $d \geq 1$).

The correct answer label $t_n$ may be set to a K-dimensional vector representing the type by the one-hot expression for the number K of types of the feature vector $x_n$. In the one-hot expression, a given element in the vector corresponds to the type of the feature vector $x_n$ and "1.0" is stored in only one element, while "0.0" is stored in all other elements. The type corresponding to the element with "1.0" is a type to be a correct answer. When a medical image based on, for example, X-rays, CT, MRI, or ultrasound is input as the feature vector $x_n$, the correct answer label $t_n$ is a true value indicating a type of disease or a prognosis (good or bad) of the patient.

It is assumed that $x_n \in R^d$ ($R^d$ represents a d-dimensional real number) is a feature vector formed of the d-dimensional real number $R^d$. A function $h^{l+1}_D$ indicating the data unit DU(l+1) is expressed by Expression (1).

$$h_D^{l+1} = f_D^l(W_D^l h_D^l) \qquad (1)$$

where $h_D^l \in \mathcal{R}^d$ represents an input/output vector of the data unit, $W_D^l \in \mathcal{R}^{d^{l+1} \times d^l}$ reoresents a learning parameter, and l=1 when $h_D^1 = x_n$ In Expression (1), a superscript l (integer that satisfies $1 \leq l \leq$) represents the hierarchical number (the same applies to the following expressions). The symbol L is an integer equal to or larger than 1, and represents the deepest hierarchical number. A symbol $f_D^l$ on the right-hand side is an activation function. Examples that can be used as the activation function include a sigmoid function, a hyperbolic tangent function (tanh function), a rectified linear unit (ReLU) function, and other such various activation functions. A matrix $W^l_D$ represents the learning parameter of the data unit DUl A vector $h^l_D$ on the right-hand side is an input vector input to the data unit DUl, namely, an output vector from the data unit DUl in the previous stage. When the number l of tiers is 1, an output vector $h^1_D$ from the data unit DU1 is $h^1_D = x_n$.

The data unit DU1 holds the feature vector $x_n$ as test data at the time of prediction performed by the prediction module 362.

A reporting unit RUl (2≤l≤L) receives input of the output vector $h^l_D$ from the data unit DUl in the same tier, and reduces the number of dimensions of the relevant output vector $h^l_D$. A function $h^l_R$ indicating the reporting unit RUl is expressed by Expression (2).

$$h_R^l = \sigma(W_R^l h_D^l) \tag{2}$$

In Expression (2), the matrix $W^l_R$ is a learning parameter of the reporting unit RUl. The d-dimensional output vector $h^l_D$ from the data unit DUl has the number of dimensions reduced to obtain an m-dimensional output vector $h^l_R$ by Expression (2). In addition, σ represents a sigmoid function.

A harmonizing unit HUl (2≤l≤L) is provided between the data unit DUl in the intermediate layer and the reallocation unit RAU for each of the data units DUl in the intermediate layer. The harmonizing unit HUl performs conversion so that the numbers of dimensions of the output pieces of data from the data units DUl in the intermediate layer become the same. Therefore, the harmonizing unit HUl inputs pieces of data with the number of dimensions of the same size to the reallocation unit RAU.

The harmonizing unit HUl receives input of the output vector $h^l_D$ from the data unit DUl in the same tier, and converts the number of dimensions of the output vector $h^l_D$ into the number of dimensions of the same size. A function $h^l_H$ indicating the harmonizing unit HUl is expressed by Expression (3).

$$h_H^l = f_H(W_H^l h_D^l) \tag{3}$$

where $W_H^l \in \mathcal{R}^{v \times d_l}$ represents a learning parameter.

In Expression (3), the matrix $W^l_H$ is a learning parameter 365 of the harmonizing unit HUl. With this, the d-dimensional output vector $h^l_D$ from the data unit DUl has the number of dimensions converted to obtain an v-dimensional output vector $h^l_H$ by Expression (3). In addition, $f_H$ represents an activation function.

The attention unit AU uses the output vector $h^l_R$ from each reporting unit RUl to calculate a weight α for each data unit DUl. A function a indicating the attention unit AU is expressed by Expression (4).

$$\alpha = \text{softmax}(W_A h_R) \tag{4}$$

where $W_A \in \mathcal{R}^{(L-1) \times m}$ (m=(L−1)) represents a learning parameter.

In Expression (4), the matrix $W_A$ is a learning parameter of the attention unit AU. In a softmax function being one of the activation functions, a vector $h_R$ with the same dimension as the number L (L=4 in the example of Expression (5)) of tiers is calculated. As expressed by Expression (5), the vector $h_R$ on the right-hand side of Expression (4) is a vector obtained by stacking $h^l_R$ in a vertical direction.

$$h_R = [h_R^2; \ldots ; h_R^L] \tag{5}$$

Example of L = 4

$$h_R^2 = [0, 1, 0]$$
$$h_R^3 = [0, 0, 1] \Rightarrow h_R = \begin{bmatrix} 0 \\ 1 \\ 0 \\ 0 \\ 0 \\ 1 \\ 1 \\ 0 \\ 0 \end{bmatrix} \begin{matrix} \} h_R^2 \\ \\ \} h_R^3 \\ \\ \} h_R^4 \end{matrix}$$
$$h_R^4 = [1, 0, 0]$$

Therefore, the matrix $W_A$ is a matrix having L rows and M columns (where M represents the number of elements in the vector $h_R$). When the softmax function is employed as the attention unit AU, each of the elements in the vector $h_R$ having the number L of tiers (the sum of all the elements is 1) expresses the weight for the corresponding data unit DUl.

The reallocation unit RAU rearranges the feature vectors $x_n$ in a given feature space into another feature space. Specifically, for example, as illustrated in FIG. 2, when the prediction model obtained from a feature vector group in the feature space SP1 is non-linear, the reallocation unit RAU relocates the feature vector group into the feature space SP2 so as to obtain a linear prediction model in the feature space SP2. A function $h^l_H$ indicating the reallocation unit RAU is expressed by Expression (6).

$$h_T^l = f_T(h_H^l, z_n) \tag{6}$$

Examples that can be used as a function $f_T$ include a Hadamard product between vectors and element addition. In this embodiment, the Hadamard product is used as expressed by Expression (7). In Expression (7), a Hadamard product between the output vector $h^l_R$ from the harmonizing unit HUl and the explainable vector $z_n$ is used.

$$h_T^l = h_H^l \odot z_n \tag{7}$$

The unifying unit UU unifies the output vector $h^l_T$ from the reallocation unit RAU and an output vector α from the attention unit AU with each other. In other words, the unifying unit UU uses the output vector α from the attention unit AU to assign weights to the output vector $h^l_T$ from the reallocation unit RAU. A function $h_U$ indicating the unifying unit UU is expressed by Expression (8).

$$h_U = \sum_{k=1}^{L-1} \alpha[k] h_T^{k+1} \tag{8}$$

In Expression (8), α[k] on the right-hand side represents a k-th dimension element of (weight for) the output vector α in Expression (4).

The decision unit DCU determines a predicted value $y_n$. Specifically, for example, the decision unit DCU assigns weights to an output vector $h_U$ from the unifying unit UU with the weight vector $w_o$ being one of the learning parameters 365, and supplies the sigmoid function σ therewith, to thereby obtain the predicted value $ya_n$. A function $ya_n$ indicating the decision unit DCU is expressed by Expression (9). In Expression (9), t included in a term $w_o^t$ means transposition.

$$ya_n = \sigma(w_o^t h_U) \tag{9}$$

The importance unit IU calculates the importance vector $s^l_n$ indicating the importance of the item of the feature in each layer of the neural network NN. A function $s_n^l$ indicating the importance unit IU is expressed by Expression (10).

$$s_n^l = \alpha[l] f_T(w_o, h_H^l) \quad (10)$$

In Expression (10), α[l] of the right-hand side represents the element in (weight for) an l-th tier of the output vector α in Expression (4). In the same manner as in Expression (6), a Hadamard product between vectors and element addition can be used as the function $f_T$. In this embodiment, the Hadamard product is used. In Expression (10), a Hadamard product between the weight vector $w_o$ and the output vector $h_H^l$ from the harmonizing unit HUl is used. The importance vector $s_n^l$ is importance in the tier l of an n-th feature vector $x_n$.

<Example of Functional Components of Neural Network NN>

Figure 5:
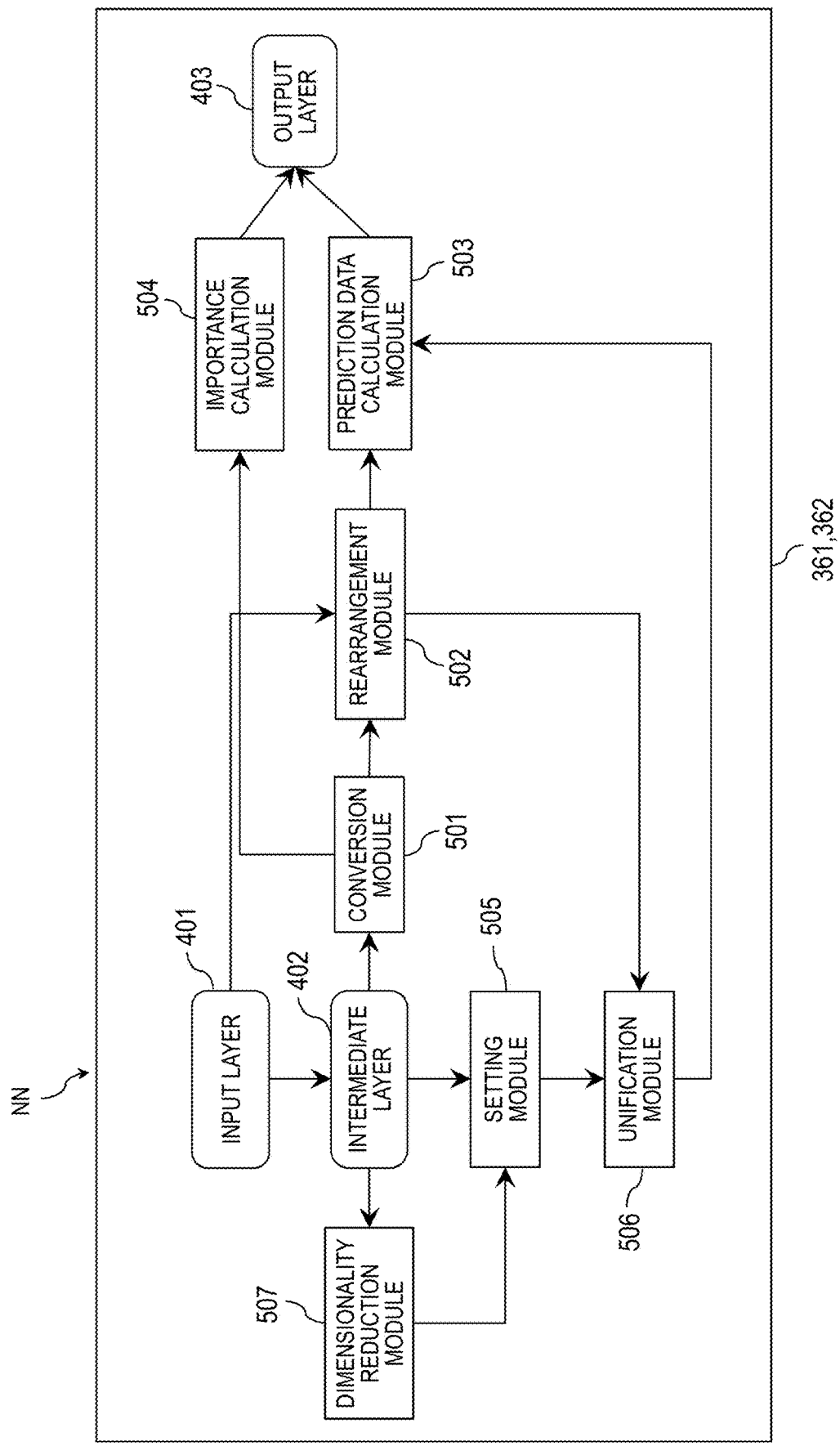
FIG. 5 is a block diagram for illustrating an example of functional components of the neural network.

FIG. 5 is a block diagram for illustrating an example of functional components of the neural network NN. The neural network NN includes the input layer 401, the intermediate layer 402, an output layer 403, a conversion module 501, a rearrangement module 502, a prediction data calculation module 503, an importance calculation module 504, a setting module 505, a unification module 506, a dimensionality reduction module 507, and a selection module 508. Those are examples of internal components of the learning module 361 and the prediction module 362.

The conversion module 501 reduces the numbers d of dimensions of the output vectors $h_D^l$ based on the output vectors $h_D^l$ from the respective data units DUl (l≥2) in the intermediate layer and a matrix $W_H^l$ as expressed by Expression (3) to output the output vector $h_H^l$ subjected to the conversion. The conversion module 501 corresponds to the above-mentioned harmonizing unit group HU.

The rearrangement module 502 rearranges the feature vectors $x_n$ in the feature space SP1 into the second feature space SP2 based on the output vector $h_H^l$ subjected to the conversion from the conversion module 501 and the feature vectors $x_n$ in the feature space SP1 supplied to the input layer 401 as expressed by Expressions (6) and (7). The rearrangement module 502 corresponds to the above-mentioned reallocation unit RAU.

The prediction data calculation module 503 calculates the predicted vectors $y_n$ for the feature vectors $x_n$ in the feature space SP1 based on the rearrangement result $h_T^l$ obtained by the rearrangement module 502 and the weight vector $w_o$ as expressed by Expression (9). The prediction data calculation module 503 corresponds to the above-mentioned decision unit DCU.

The importance calculation module 504 calculates the importance vector $s_n^l$ of the feature vector $x_n$ in the tier l in the intermediate layer 402 based on the output vector $h_H^l$ subjected to the conversion and the weight vector $w_o$ as expressed by Expression (10). The importance calculation module 504 corresponds to the above-mentioned importance unit IU.

For example, it is assumed that, when the feature vector $x_n$ indicates a diagnostic image, an output vector $h_D^{la}$ in a given tier la is a feature indicating whether or not a given subject has a shape that fits a cancer tissue, and an output vector $h_D^{lb}$ in a given tier lb (≠la) is a feature indicating whether or not the given subject has a pattern that fits a cancer tissue. In this case, reference to the corresponding importance vectors $s_n^{la}$ and $s_n^{lb}$ allows the user to explain which feature of the subject in the diagnostic image has been taken into consideration by the neural network NN in determining the subject as a cancer tissue. For example, when the importance vector $s_n^{la}$ is low but the importance vector $s_n^{lb}$ is high, the user can explain that the neural network NN has determined the subject as a cancer tissue in consideration of the pattern of the subject in the relevant image $x_n$.

The setting module 505 sets the weight α for the intermediate layer 402 based on the output vector $h_D^l$ of the intermediate layer 402 and the matrix $W_A$ as expressed by Expressions (4) and (5). The setting module 505 corresponds to the above-mentioned attention unit AU.

The unification module 506 unifies the rearrangement result $h_T^l$ and the weight α set by the setting module 505 as expressed by Expression (8). The unification module 506 corresponds to the above-mentioned unifying unit UU. In this case, the prediction data calculation module 503 calculates the predicted vectors $y_n$ based on a unification result $h_u$ obtained by the unification module 506 and the weight vector $w_o$. The importance calculation module 504 also calculates the importance vector $s_n^l$ based on the weight α set by the setting module 505, the output vector $h_H^l$ subjected to the conversion, and the weight vector $w_o$.

The dimensionality reduction module 507 reduces the number d of dimensions of the output vector $h_D^l$ based on the output vector $h_D^l$ from the intermediate layer 402 and the matrix $W_R^l$ as expressed by Expression (2) to output the output vector $h_R^l$ subjected to the dimensionality reduction. The dimensionality reduction module 507 corresponds to the above-mentioned reporting unit group RU. In this case, the setting module 505 sets the weight α for the intermediate layer 402 based on the output vector $h_R^l$ subjected to the dimensionality reduction from the dimensionality reduction module 507 and the matrix $W_A$.

When the learning module 361 is supplied with training data including the feature vectors $x_n$ in the feature space SP1 and the correct answer labels $t_n$ for the predicted vectors $y_n$, the learning module 361 uses the predicted vectors $y_n$ and the correct answer labels $t_n$ to optimize the matrix $W_D^l$ being a first learning parameter, the matrix $W_H^l$ being a second learning parameter, the weight vector $w_o$ being a third learning parameter, the matrix $W_A$ being a fourth learning parameter, and the matrix $W_R^l$ being a fifth learning parameter so as to minimize, for example, a cross entropy between the correct answer labels $t_n$ and the predicted values $y_n$.

The prediction module 362 sets the optimized learning parameters 365 for the neural network NN, and supplies the input layer 401 with a feature vector $x_n^l$ as test data, to thereby cause the prediction data calculation module 503 to finally calculate a predicted vector $y_n^l$.

<Example of Procedures for Learning Processing and Prediction Processing>

Figure 6:
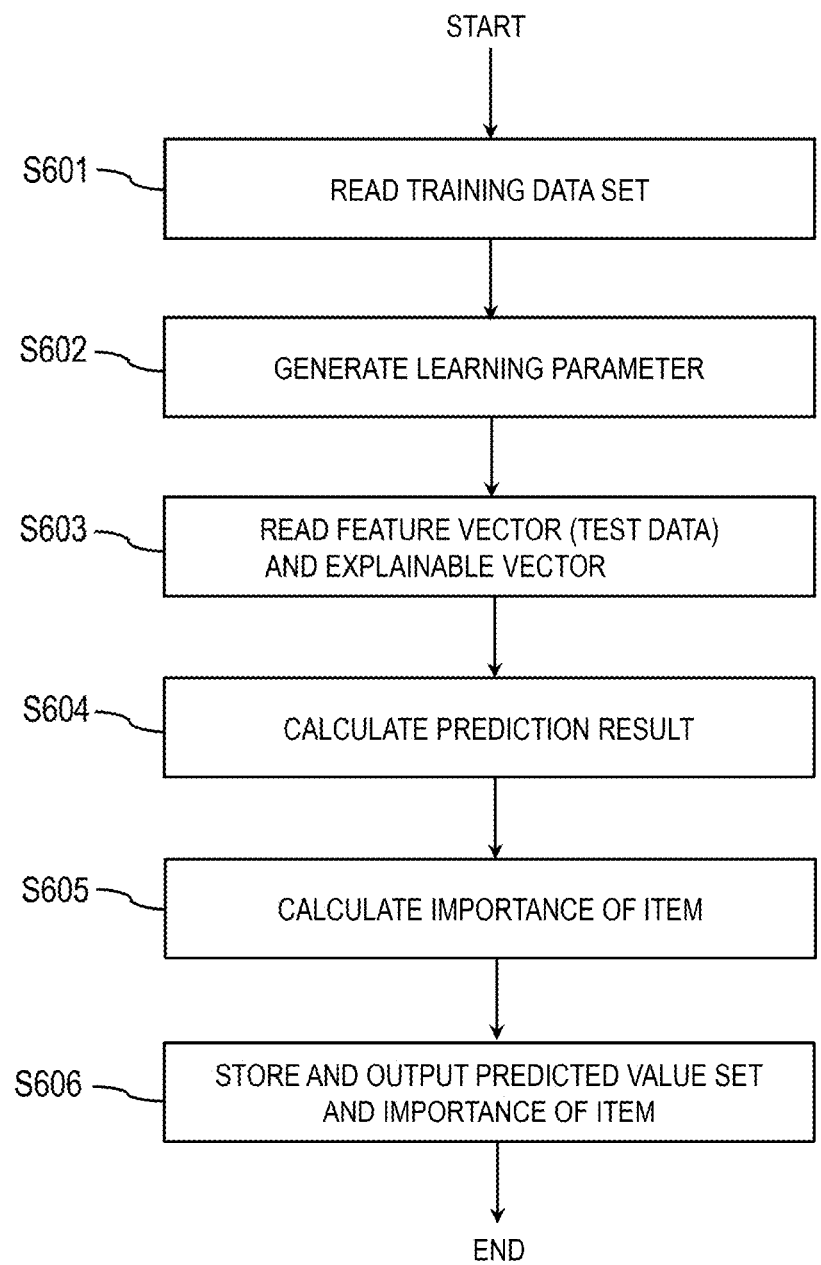
FIG. 6 is a flow chart for illustrating an example of procedures for learning processing and predictive processing based on the neural network NN.

FIG. 6 is a flow chart for illustrating an example of procedures for learning processing and predictive processing based on the neural network NN. In FIG. 6, Step S601 and Step S602 correspond to the learning processing performed by the learning module 361, and Step S603 to Step S607 correspond to the predictive processing performed by the prediction module 362. First, the analysis apparatus 320 reads the training data set 364 (Step S601).

The analysis apparatus 320 performs learning by supplying the neural network NN with the training data $\{x_n \text{ and } t_n\}$, and generates the learning parameters 365 (matrix $W_D^l$, matrix $W_R^l$, matrix $W_H^l$, matrix $W_A$, and weight vector $w_o$) (Step S602). In the learning (Step S602), for example, the learning module 361 uses a statistical gradient method to optimize the learning parameters 365 so as to minimize a cross entropy between the correct answer labels $t_n$ and the predicted values $ya_n$. The analysis apparatus 320 stores the generated learning parameters 365 in the server DB 363.

Subsequently, the analysis apparatus 320 reads the feature vector $x_n$ serving as test data and the explainable vector $z_n$ (Step S603), supplies the read data to the neural network NN (prediction model) in which the learning parameters 365 have been reflected, uses Expression (9) to calculate the predicted value $ya_n$ as the prediction result 353 (Step S604), and uses Expression (10) to calculate the importance vector $s'_n$ indicating the importance of the item (Step S605).

Then, the analysis apparatus 320 stores the prediction result 353 and the importance vector $s'_n$, and outputs the prediction result 353 to the client terminal 300 (Step S606). The client terminal 300 displays the prediction result 353 and the importance vector $s'_n$ on the monitor 305. In this manner, according to the neural network NN, the importance $s'_n$ can be obtained for the feature vector $x_n$ being sample data, which can enhance interpretability of the prediction result 353. Further, the linear prediction model is obtained through preliminary rearrangement of samples (feature vectors $x_n$), and hence a predicted value can be calculated highly accurately with light load at the time of learning and at the time of prediction.

<Example of Functional Components of Analysis Apparatus 320>

Figure 7:
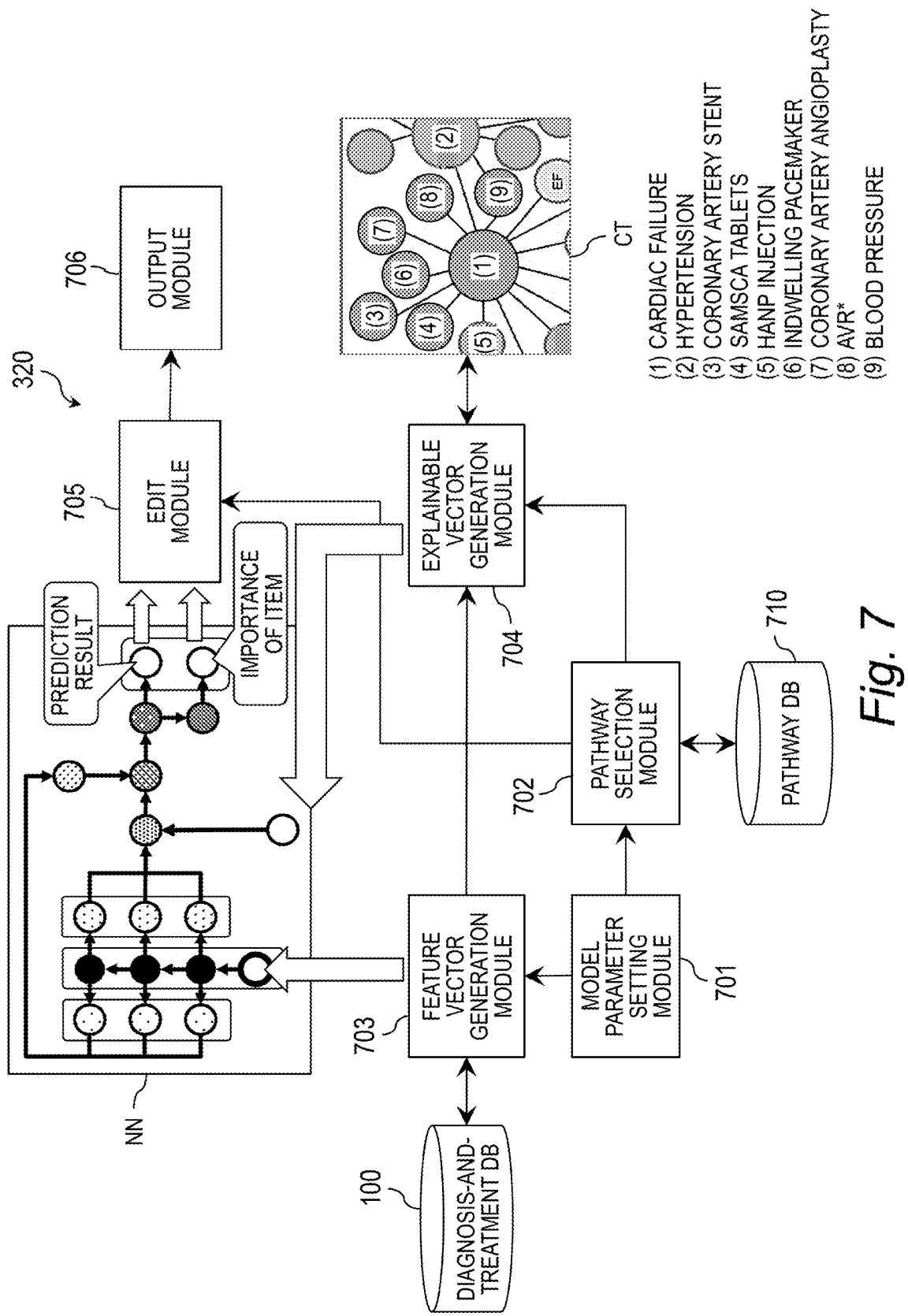
FIG. 7 is a block diagram for illustrating an example of functional components of the analysis apparatus.

FIG. 7 is a block diagram for illustrating an example of functional components of the analysis apparatus 320. The analysis apparatus 320 includes a model parameter setting module 701, a pathway selection module 702, a feature vector generation module 703, an explainable vector generation module 704, an edit module 705, and an output module 706. Those components have their functions implemented by causing the processor 323 to execute a program stored in the HDD 321, the memory 322, or other such storage device. In addition, the neural network NN, the diagnosis-and-treatment DB 100, a pathway DB 710, and the clinical terminology CT may be provided to the analysis apparatus 320, or may be stored in an external apparatus (not shown) that enables communication to/from the analysis apparatus 320 via the network 310.

The pathway DB 710 is a database configured to store the clinical pathway CP. A non-computer-readable clinical pathway indicating medical rules is converted into the clinical pathways CP having a computer readable format by an XML/JSON converter in advance, and stored in the pathway DB 710. In the same manner, the guidelines or other such medical electronic documents are also converted into the clinical pathways CP with a word vector having a computer readable format by a Word2Vec converter, and stored in the pathway DB 710.

The model parameter setting module 701 sets the model parameter MP. Specifically, for example, the monitors 305 and 325 are caused to display a selection screen for the model parameter MP, and the user operates the input apparatus 304 and 324 to select the model parameter MP, to thereby set the model parameter MP. In addition, as the model parameter MP, the model parameter MP supplied from the external apparatus (not shown) via the network 310 may be set.

The pathway selection module 702 uses the model parameter MP set by the model parameter setting module 701 as a search key to select the corresponding clinical pathway CP from the pathway DB 710. Specifically, for example, the pathway selection module 702 selects the clinical pathway CP corresponding to the prediction target model PTM set in the model parameter MP from the pathway DB 710. When a plurality of clinical pathways CP have been selected, the pathway selection module 702 may output the plurality of clinical pathways CP to the monitors 305 and 325 to cause the user to make a selection therefrom. In another case, when a plurality of clinical pathways CP have been selected, the pathway selection module 702 may select the clinical pathway CP set as graphic data with a higher priority than the clinical pathway CP set as text data representing at least one sentence, or may preferentially select the clinical pathway CP having a shorter pathway from the prediction starting point to the prediction target.

The feature vector generation module 703 refers to the diagnosis-and-treatment DB 100 to generate the feature vector $x_n$ based on the model parameter MP. At the time of learning based on the neural network NN, the feature vector generation module 703 generates the feature vectors $x_n$ for an indefinitely large number of patients as the training data set 364, and supplies the feature vectors $x_n$ to the neural network NN. At the time of prediction based on the neural network NN, the feature vector generation module 703 generates the feature vector $x_n$ for a specific patient, and supplies the feature vector $x_n$ to the neural network NN.

The explainable vector generation module 704 generates the explainable vector $z_n$ based on the feature vectors $x_n$ generated by the feature vector generation module 703 and the clinical pathway selected by the pathway selection module 702 (selected clinical pathway). Details of processing for generation of the explainable vector $z_n$ are described later with reference to FIG. 8.

The edit module 705 uses the prediction result 353 and the importance of the item, which have been output from the neural network NN, to edit the selected clinical pathway CP. Details of the edit performed by the selected clinical pathway CP are described later with reference to FIG. 10 to FIG. 14.

The output module 706 outputs an edit result obtained through the edit performed by the edit module 705. Specific examples of an output destination of the edit result include the HDDs 301 and 321, the memories 302 and 322, the monitors 305 and 325, and the external apparatus (not shown) that is capable of communicating to/from via the network 310. A screen for presenting the edit result is displayed on the monitors 305 and 325 as illustrated in FIG. 10 to FIG. 14. This allows the doctor being the user to verify a reason and a basis for the highly accurate prediction result 353.

<Example of Generation of Explainable Vector>

Figure 8:
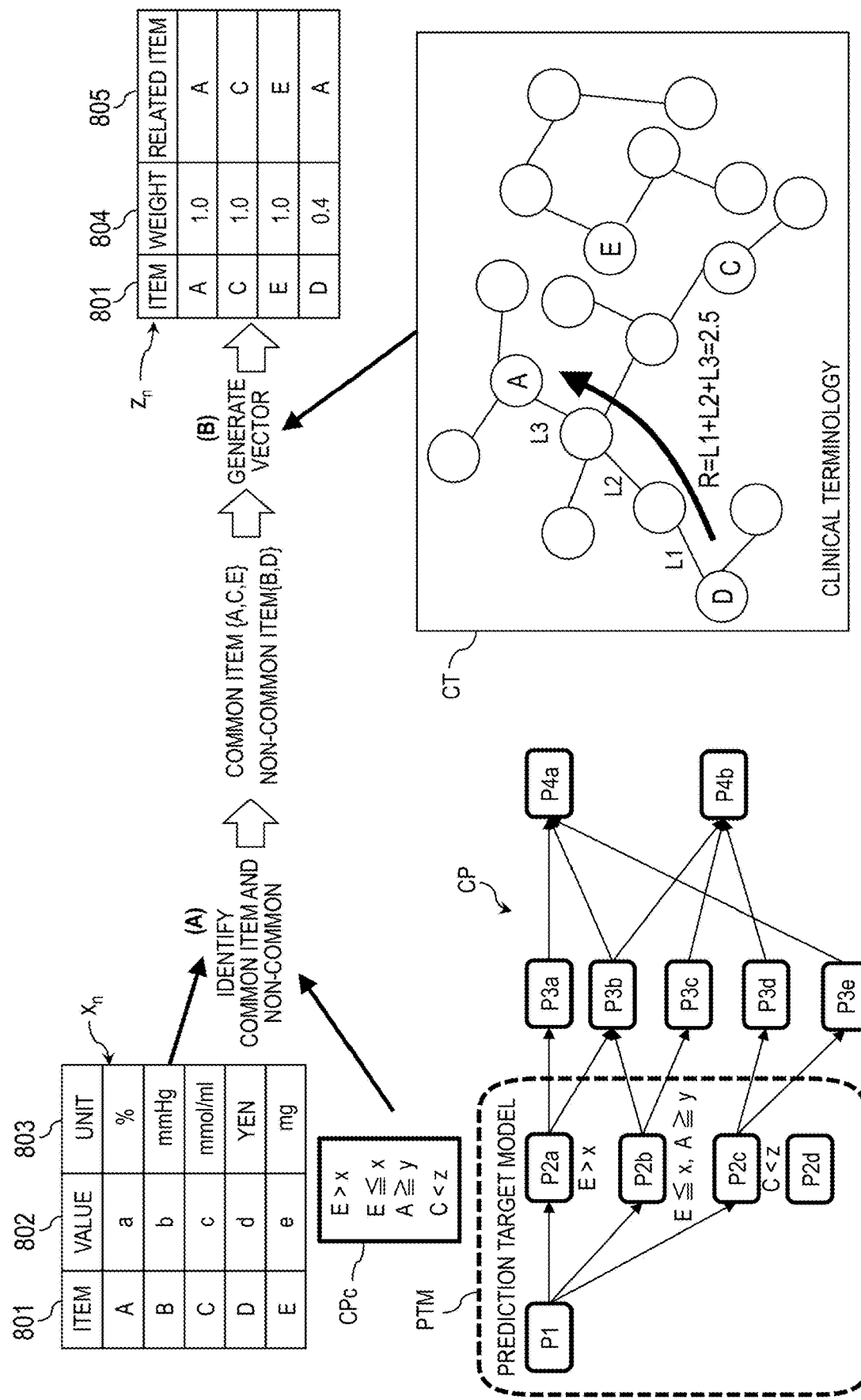
FIG. 8 is an explanatory diagram for illustrating an example of processing for generation of the explainable vector performed by the explainable vector generation module.

FIG. 8 is an explanatory diagram for illustrating an example of processing for generation of the explainable vector $z_n$ performed by the explainable vector generation module 704. The feature vector the model parameter MP (prediction target model PTM and prediction parameter), and the clinical pathway branch criteria CPc are used in the generation 103 of the explainable vector $z_n$. As described above, the feature vector $x_n$ includes an item 801, a value 802, and a unit 803.

In part (A), the explainable vector generation module 704 compares the item 801 of the feature vector $x_n$ with the clinical pathway branch criteria CPc to identify a common item and a non-common item. The item 801 includes "A", "B", "C", "D", and E. Meanwhile, the clinical pathway branch criteria CPc include "A", "C", and E. Therefore, the common items are "A", "C", and "E", and the non-common items are "B" and D.

In part (B), the explainable vector generation module 704 uses the clinical terminology CT to identify a related item 805 relating to each item 801, and calculates a weight 804 of each item 801 to generate the explainable vector $z_n$. The related item 805 is an item indicating the relevance between the item 801 and the clinical terminology CT, and the weight 804 has a value indicating the degree of the relevance.

When there is a common item included in the clinical terminology CT, the weight 804 of the common item is "1.0", and the related item 805 of the common item is the same item as the item 801. However, when there is no common item included in the clinical terminology CT, the weight 804 of the common item is "0.0", and the related item 805 of the common item is "not available". Therefore, the related items 805 of the common items "A", "C", and "E" are "A", "C", and "E", respectively, and the weight 804 of each of the common items is "1.0".

In regard to the non-common item, when there is a non-common item included in the clinical terminology CT, the explainable vector generation module 704 calculates a relevance degree R indicating the relevance between the non-common item and the common item in the clinical terminology CT. The relevance degree R is the shortest distance from the non-common item to the common item. The clinical terminology CT is information indicating medical terms and the relevance therebetween as described above, and is, for example, network information using the medical terms as nodes and the relevance as a link. The link indicates the relevance between medical terms located at both ends of the link. The relevance is expressed by, for example, the link length. The shorter link length indicates the higher relevance degree.

When the non-common item "D" is taken as an example, the common item "A" is reached via links L1, L2, and L3. When it is assumed that the links L1, L2, and L3 each represent a link length, the relevance degree R is expressed by the following expression.

$$R=L1+L2+L3$$

In this example, it is assumed that R=2.5. The weight 804 of the non-common item "D" is the reciprocal of the relevance degree R (1/R=0.4), and the related item 805 is A. Therefore, as the distance to the common item becomes shorter, the weight 804 becomes higher. With this setting, the importance of each item 801 can be objectively verified by being converted into a numerical value with the clinical terminology CT based on the weight 804 of each item 801. The basis for the weight 804 can also be objectively verified with the clinical terminology CT based on the related item 805.

<Example of Sequence of Analysis>

Figure 9:
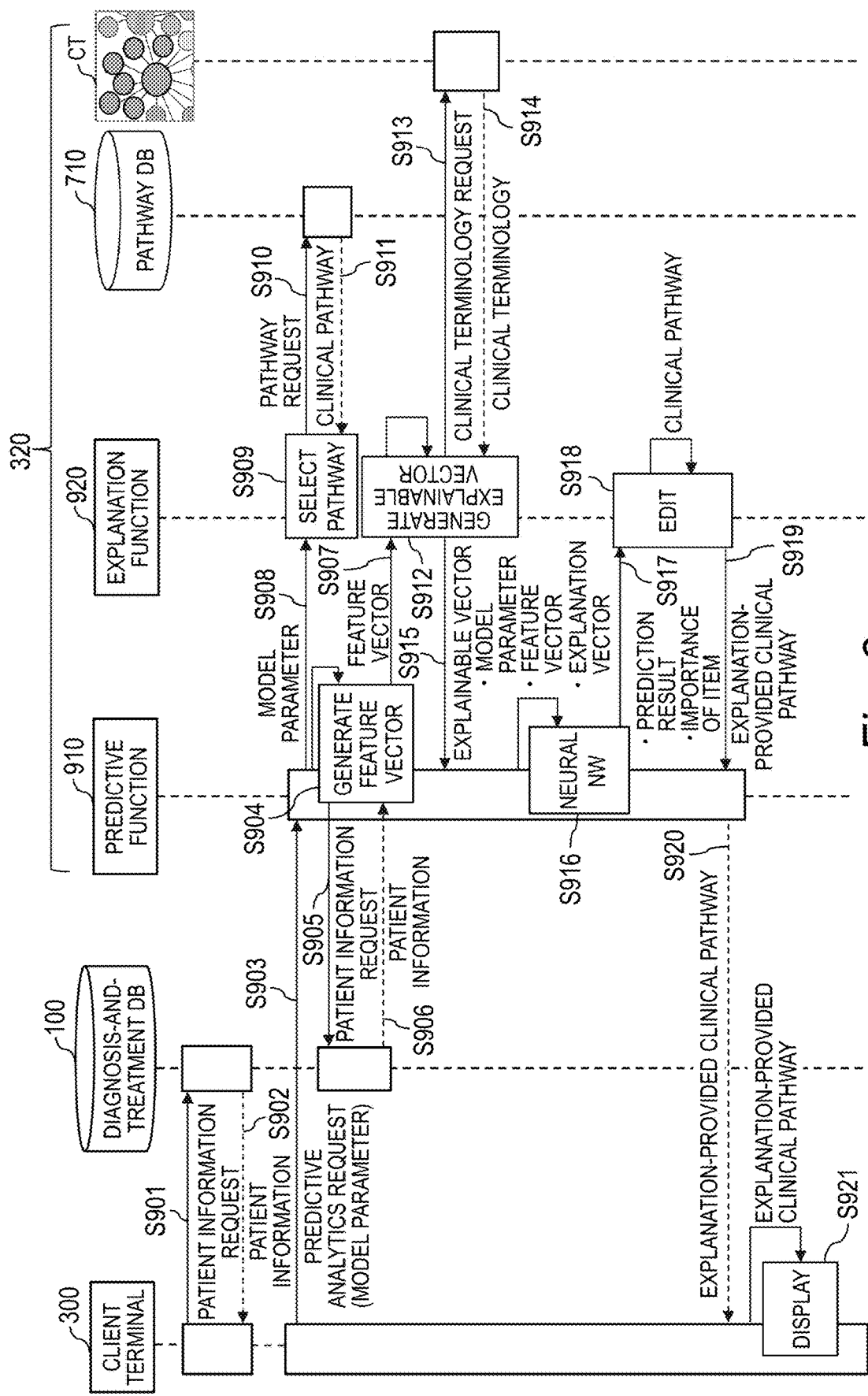
FIG. 9 is a sequence diagram for illustrating an example of a sequence of analyses performed by the analysis apparatus.

FIG. 9 is a sequence diagram for illustrating an example of a sequence of analyses performed by the analysis apparatus 320. It is assumed that the neural network NN already has the learning model generated by the training data set 364. In addition, in order to simplify the description, the analysis apparatus 320 is assumed to have the pathway DB 710 and the clinical terminology CT.

The client terminal 300 transmits a patient information request to the diagnosis-and-treatment DB 100 (Step S901), and the diagnosis-and-treatment DB 100 returns patient information corresponding to the patient information request to the client terminal 300 (Step S902). This allows the user of the client terminal 300 to view the patient information on the monitor 305.

The client terminal 300 uses the patient information acquired through a user operation to create a predictive analytics request including the model parameter MP, and transmits the predictive analytics request to the analysis apparatus 320 (Step S903). When receiving the predictive analytics request, a predictive function 910 of the analysis apparatus 320 causes the feature vector generation module 703 to generate the feature vector $x_n$ (Step S904). Specifically, for example, the predictive function 910 transmits a patient information request to the diagnosis-and-treatment DB 100 (Step S905), and refers to the diagnosis-and-treatment DB 100 to acquire the patient information corresponding to the patient information request (Step S906).

Then, the predictive function 910 causes the feature vector generation module 703 to generate the feature vector $x_n$ through use of the model parameter MP and the patient information, and outputs the generated feature vector $x_n$ to an explanation function 920 of the analysis apparatus 320 (Step S907). The predictive function 910 also outputs the model parameter MP in the predictive analytics request to the explanation function 920 (Step S908).

The explanation function 920 causes the pathway selection module 702 to select the clinical pathway CP as an edit target (Step S909). Specifically, for example, the explanation function 920 generates a pathway request based on the model parameter MP, outputs the pathway request to the pathway DB 710 (Step S910), and acquires the corresponding clinical pathway CP from the pathway DB 710 (Step S911).

Then, the explanation function 920 causes the explainable vector generation module 704 to generate the explainable vector $z_n$ based on the feature vector $x_n$ and the selected clinical pathway CP (Step S912). Specifically, for example, the explanation function 920 transmits a clinical terminology request to the clinical terminology CT (Step S913), and acquires the clinical terminology CT (Step S914). The explanation function 920 uses the clinical terminology CT to generate the explainable vector $z_n$, and outputs the explainable vector to the predictive function 910 (Step S915).

The predictive function 910 executes the predictive processing based on the neural network NN (Step S916). Specifically, for example, the predictive function 910 selects the corresponding neural network NN from among the neural network group NNs based on the model parameter MP. Then, the predictive function 910 calculates the prediction result 353 and the importance of the item by supplying the selected neural network NN with the feature vector $x_n$ and the explainable vector and outputs the prediction result 353 and the importance of the item to the explanation function 920 (Step S917).

The explanation function 920 causes the edit module 705 to edit the clinical pathway CP (Step S918). Specifically, for example, the explanation function 920 generates the explanation-provided clinical pathway CPe by supplying the clinical pathway CP with the prediction result 353 and the importance of the item, and returns the explanation-provided clinical pathway CPe to the predictive function 910 (Step S919). The predictive function 910 transmits the explanation-provided clinical pathway CPe to the client terminal 300 (Step S920). The client terminal 300 displays the received explanation-provided clinical pathway CPe on the monitor 305 (Step S921). This allows the doctor being the user to verify a reason and a basis for the highly accurate prediction result 353.

<Screen Examples>

Next, with reference to FIG. 10 to FIG. 14, screen examples for displaying the explanation-provided clinical pathway CPe created by the edit module 705 are described, and details of the edit processing performed on the clinical pathway by the edit module 705 are also described.

Figure 10:
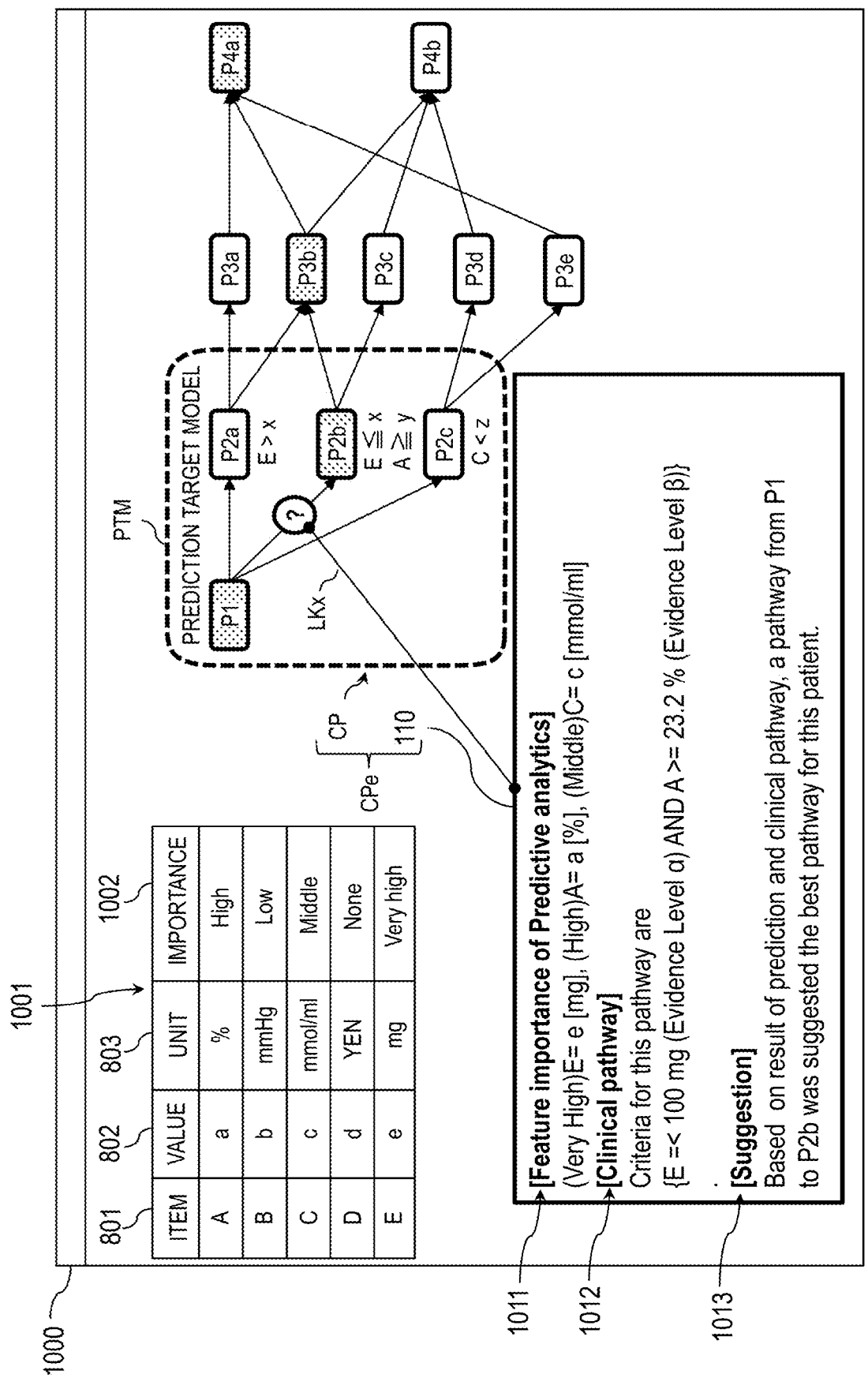
FIG. 10 is an explanatory diagram for illustrating a screen example (Case 1) for displaying the explanation-provided clinical pathway.

FIG. 10 is an explanatory diagram for illustrating a screen example (Case 1) for displaying the explanation-provided clinical pathway CPe. Case 1 is a case in which the prediction result 353 of the neural network NN and the prediction target of the clinical pathway CP match each other. A screen of Case 1 is referred to as "first screen 1000".

The first screen 1000 is a screen for displaying importance data 1001 and the explanation-provided clinical pathway CPe. The importance data 1001 is data obtained by associating the item, value, and unit of the feature vector $x_n$ with the importance of the item. In this example, the importance of the item has 5 levels of "Very high", "High", "Middle", "Low", and "None", but may be equal to or lower than 4 levels or equal to or higher than 6 levels as long as the importance has 2 or more levels. The importance of the item may be also expressed by a numerical value. In Case 1, the feature vector $x_n$ satisfies the criteria of E≤100 (mg) and A≥23.2(%) in the clinical pathway branch criteria CPc, and hence the importance degrees "Very high" and "High" of the item E and an item A are higher than the importance degrees of the other items.

The explanation-provided clinical pathway CPe is information obtained by associating the clinical pathway CP and the explanation information 110 with each other by the link LKx. The explanation information 110 includes predictive analytics information 1011 relating to the importance of the feature, clinical pathway information 1012, and suggestion information 1013, and is created by the edit module 705.

The predictive analytics information 1011 is information obtained by associating the value and the importance with each other for each item. The clinical pathway information 1012 indicates the clinical pathway branch criteria CPc satisfied by the value of the item in the feature vector $x_n$. In Case 1, it is indicated that the feature vector $x_n$ satisfies E≤x (mg) and A≥y (%) in the clinical pathway branch criteria CPc relating to the treatment P2b.

The suggestion information 1013 is information for suggesting a pathway recommended in the prediction target model PTM. In Case 1, it is assumed that the treatment P2b has the highest treatment efficacy probability in the prediction result 353. Therefore, the edit module 705 sets a pathway from the symptom P1 to the treatment P2b as a recommended pathway, and creates character string information to that effect as the suggestion information 1013. In addition, the edit module 705 highlights the symptom P1 and the treatment P2b on the recommended pathway, and couples the recommended pathway to the explanation information 110 by the link LKx.

In this manner, in the explanation-provided clinical pathway CPe on the first screen 1000 for presenting Case 1, in regard to the patient identified by this feature vector $x_n$, the importance degrees of the item E, the item A, and an item C for the relevant patient become higher in the stated order, and the treatment P2b has the highest treatment efficacy probability for the relevant patient in the case of the symptom P1. Therefore, when selecting the treatment P2b for the relevant patient with the symptom P1, the doctor can provide an explanation by stating the items E, A, and C as the bases in the order of the importance.

Figure 11:
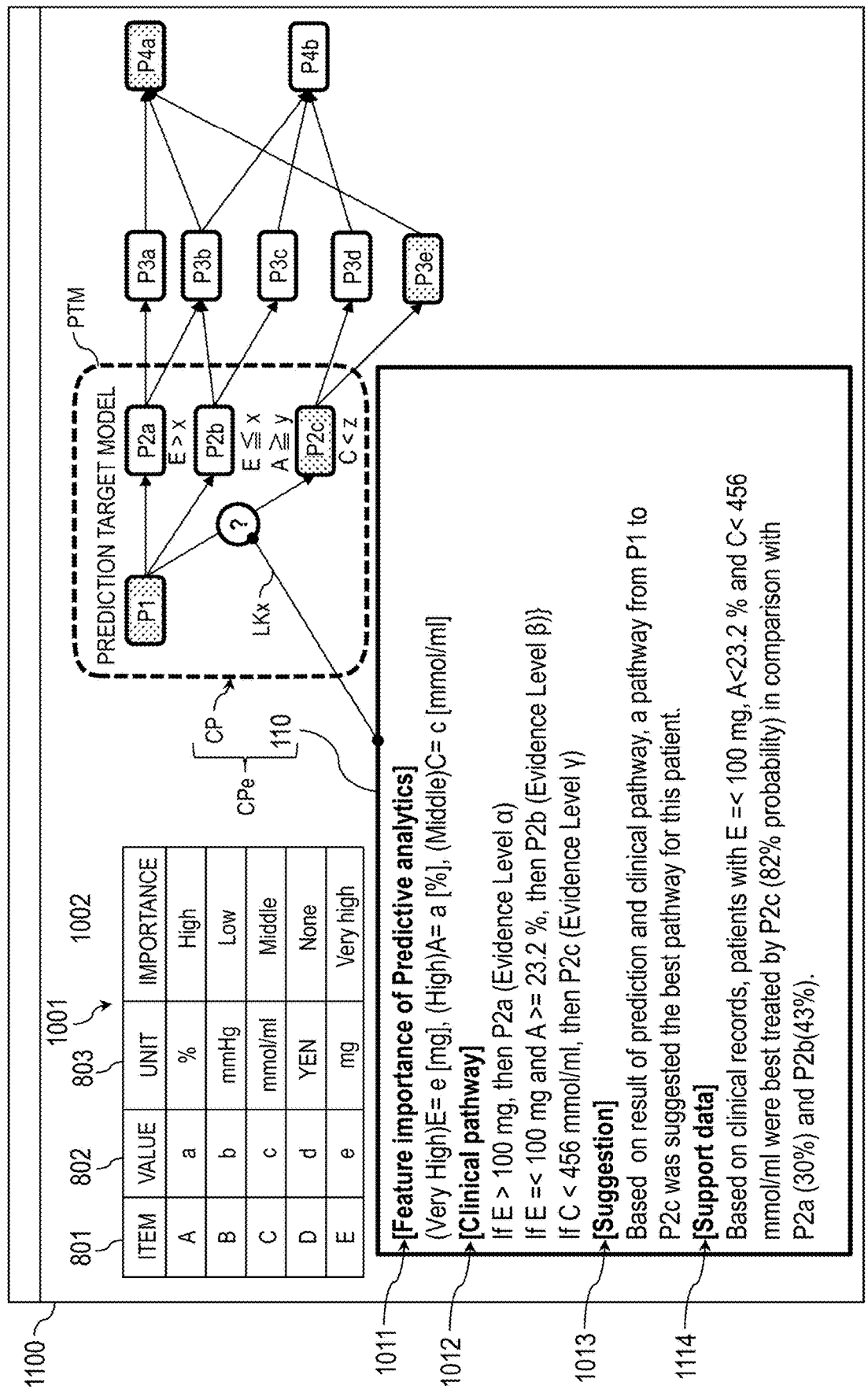
FIG. 11 is an explanatory diagram for illustrating a screen example (Case 2) for displaying the explanation-provided clinical pathway.

FIG. 11 is an explanatory diagram for illustrating a screen example (Case 2) for displaying the explanation-provided clinical pathway CPe. Case 2 is a case in which the prediction result 353 of the neural network NN and the prediction target of the clinical pathway CP do not match each other, but a pathway that can express the prediction result 353 is included in the prediction target model PTM. A screen of Case 2 is referred to as "second screen 1100".

The second screen 1100 is a screen for displaying the importance data 1001 and the explanation-provided clinical pathway CPe. In Case 2, it is assumed that the feature vector $x_n$ exhibits E≤x (mg), A<y (%), and C≥z (mmol/ml), and none of the clinical pathway branch criteria CPc is satisfied.

The explanation-provided clinical pathway CPe is information obtained by associating the clinical pathway CP and the explanation information 110 with each other by the link LKx. The explanation information 110 includes predictive analytics information 1011 relating to the importance of the feature, clinical pathway information 1012, suggestion information 1013, and support data 1114, and is created by the edit module 705.

In Case 2, the feature vector $x_n$ exhibits E≤x (mg), A<y (%), and C≥z (mmol/ml), and none of the clinical pathway branch criteria CPc is satisfied. Thus, the clinical pathway information 1012 presents the clinical pathway branch criteria CPc to be satisfied by the value of the item in the feature vector $x_n$. This allows the user to verify that the feature vector $x_n$ does not satisfy the clinical pathway branch criteria CPc.

In Case 2, it is assumed that the treatment P2c has the highest treatment efficacy probability in the prediction result 353. In regard to the suggestion information 1013, the edit module 705 therefore sets the pathway from the symptom P1 to the treatment P2c as the recommended pathway, and creates the character string information to that effect as the suggestion information 1013. In addition, the edit module 705 highlights the symptom P1 and the treatment P2c on the recommended pathway, and couples the recommended pathway to the explanation information 110 by the link LKx.

Support data 1114 supports the suggestion information 1013 to present the basis of the suggestion information 1013. The edit module 705 creates support data indicating that the feature vector $x_n$ for the patient in Case 2 exhibits E≤x (mg), A<y (%), and C≥z (mmol/ml), and in this case, the treatment P2c has the highest efficacy probability (82%) in the neural network NN.

In this manner, in the explanation-provided clinical pathway CPe on the second screen 1100 for presenting Case 2, in regard to the patient identified by this feature vector $x_n$, the feature vector $x_n$ does not correspond to any of the clinical pathway branch criteria CPc for the treatments P2a to P2c, but the neural network NN predicts that the treatment P2c has the highest treatment efficacy probability for the relevant patient. This enables the analysis apparatus 320 to point out a difference between the clinical pathway CP and the prediction result 353. Therefore, when selecting the treatment P2c for the relevant patient with the symptom P1, the doctor can provide an explanation by stating the items E, A, and C as the bases for the selection in the order of the importance. In addition, the accumulation of such cases can contribute to, for example, review of the clinical pathway branch criteria CPc relating to the treatment P2c and correction of the clinical pathway CP.

Figure 12:
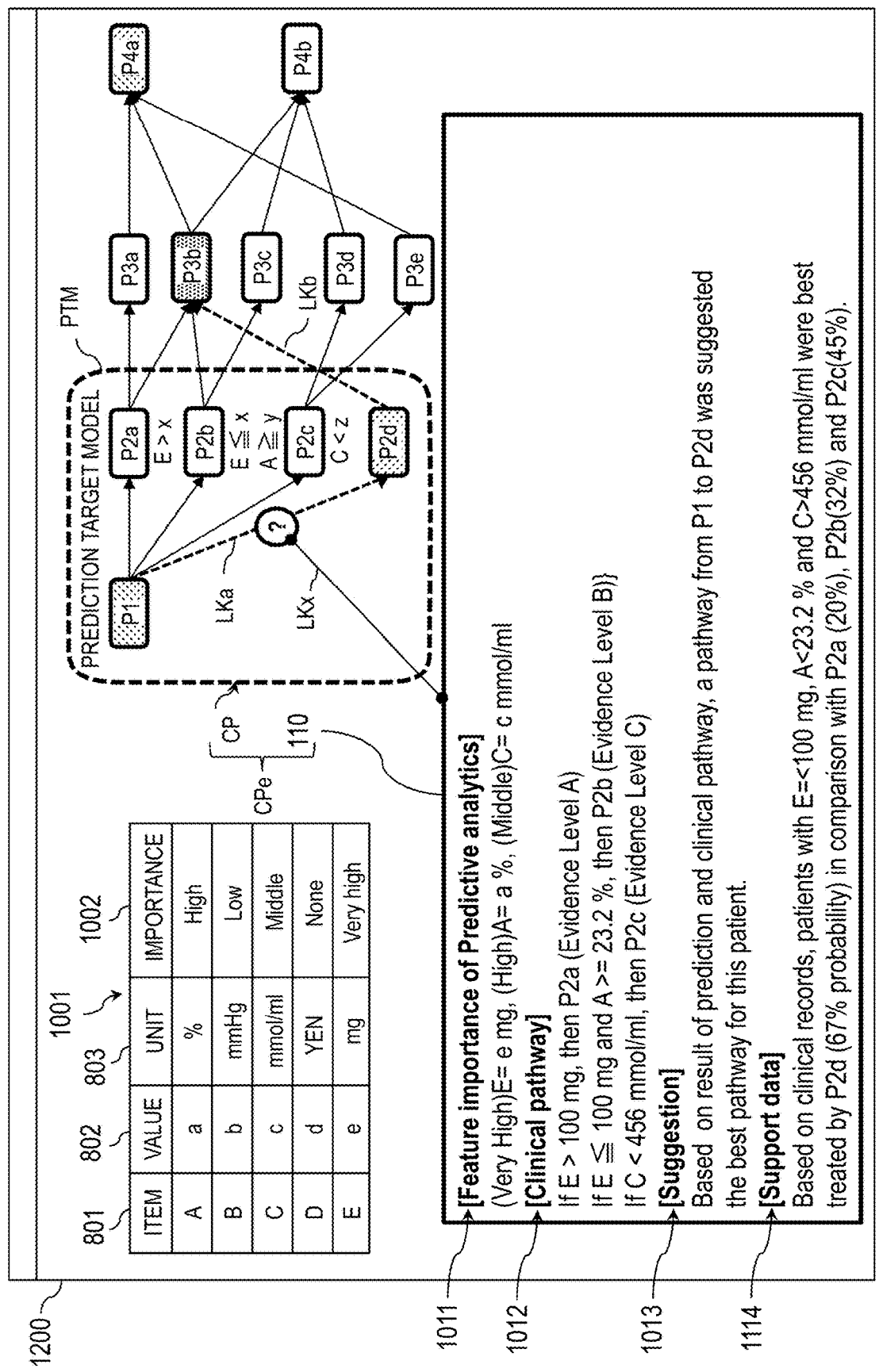
FIG. 12 is an explanatory diagram for illustrating a screen example (Case 3) for displaying the explanation-provided clinical pathway.

FIG. 12 is an explanatory diagram for illustrating a screen example (Case 3) for displaying the explanation-provided clinical pathway CPe. Case 3 is a case in which the prediction result 353 of the neural network NN and the prediction target of the clinical pathway CP do not match each other, and a pathway that can express the prediction result 353 is not included in the prediction target model PTM. A screen of Case 3 is referred to as "third screen 1200".

In Case 3, it is assumed that the treatment P2d has been added to the model parameter MP as the prediction target to select the neural network NN subjected to the learning with the treatment P2d taken into consideration in addition to the treatments P2a to P2c. The treatment P2d is not included in the clinical pathway CP, but is assumed to have been added to the model parameter MP by the user who wishes to take the treatment P2*d* into consideration as well.

The third screen 1200 is a screen for displaying the importance data 1001 and the explanation-provided clinical pathway CPe. In Case 3, in the same manner as in Case 2, it is assumed that the feature vector $x_n$ exhibits E≤x (mg), A<y (%), and C≥z (mmol/ml), and none of the clinical pathway branch criteria CPc is satisfied.

The explanation-provided clinical pathway CPe is information obtained by associating the clinical pathway CP and the explanation information 110 with each other by the link LKx. The explanation information 110 includes predictive analytics information 1011 relating to the importance of the feature, clinical pathway information 1012, suggestion information 1013, and support data 1114, and is created by the edit module 705.

In Case 3, the feature vector $x_n$ exhibits E≤x (mg), A<y (%), and C≥z (mmol/ml), and none of the clinical pathway branch criteria CPc is satisfied. Thus, the clinical pathway information 1012 presents the clinical pathway branch criteria CPc to be satisfied by the value of the item in the feature vector $x_n$. This allows the user to verify that the feature vector $x_n$ does not satisfy the clinical pathway branch criteria CPc.

In Case 3, it is assumed that the treatment P2*d* has the highest efficacy probability in the prediction result 353. In regard to the suggestion information 1013, the edit module 705 therefore sets the pathway from the symptom P1 to the treatment P2*d* as the recommended pathway, and creates the character string information to that effect as the suggestion information 1013. In addition, the edit module 705 highlights the symptom P1 and the treatment P2*d* on the recommended pathway, couples the symptom P1 to the treatment P2*d* by the link LKa, couples the treatment P2*d* to the treatment P3*b* by the link LKb, and couples the recommended pathway from the symptom P1 to the treatment P2*d* to the explanation information 110 by the link LKx.

The support data 1114 presents the basis for the suggestion information 1013. In the same manner as in Case 2, the edit module 705 creates support data indicating that the feature vector $x_n$ for the patient in Case 3 exhibits E≤x (mg), A<y (%), and C≥z (mmol/ml), and in this case, the treatment P2*d* has the highest treatment efficacy probability (67%) in the neural network NN and has a probability exceeding the probabilities of 20%, 32%, and 45% of the treatments P2*a* to P2*c* being the prediction targets.

In this manner, in the explanation-provided clinical pathway CPe on the third screen 1200 for presenting Case 3, in regard to the patient identified by this feature vector $x_n$, the feature vector $x_n$ does not correspond to any of the clinical pathway branch criteria CPc for the treatments P2*a* to P2*c*, but the neural network NN predicts that the treatment P2*d* added to the model parameter MP has the highest treatment efficacy probability for the relevant patient. This enables the analysis apparatus 320 to verify that the prediction result 353 is not included in the clinical pathway CP and to identify a new diagnosis-and-treatment pathway that is not included in the clinical pathway CP and new clinical pathway branch criteria CPc therefor. Therefore, when selecting the treatment P2*d* for the relevant patient with the symptom P1, the doctor can provide an explanation by stating the items E, A, and C as the bases for the selection in the order of the importance.

Figure 13:
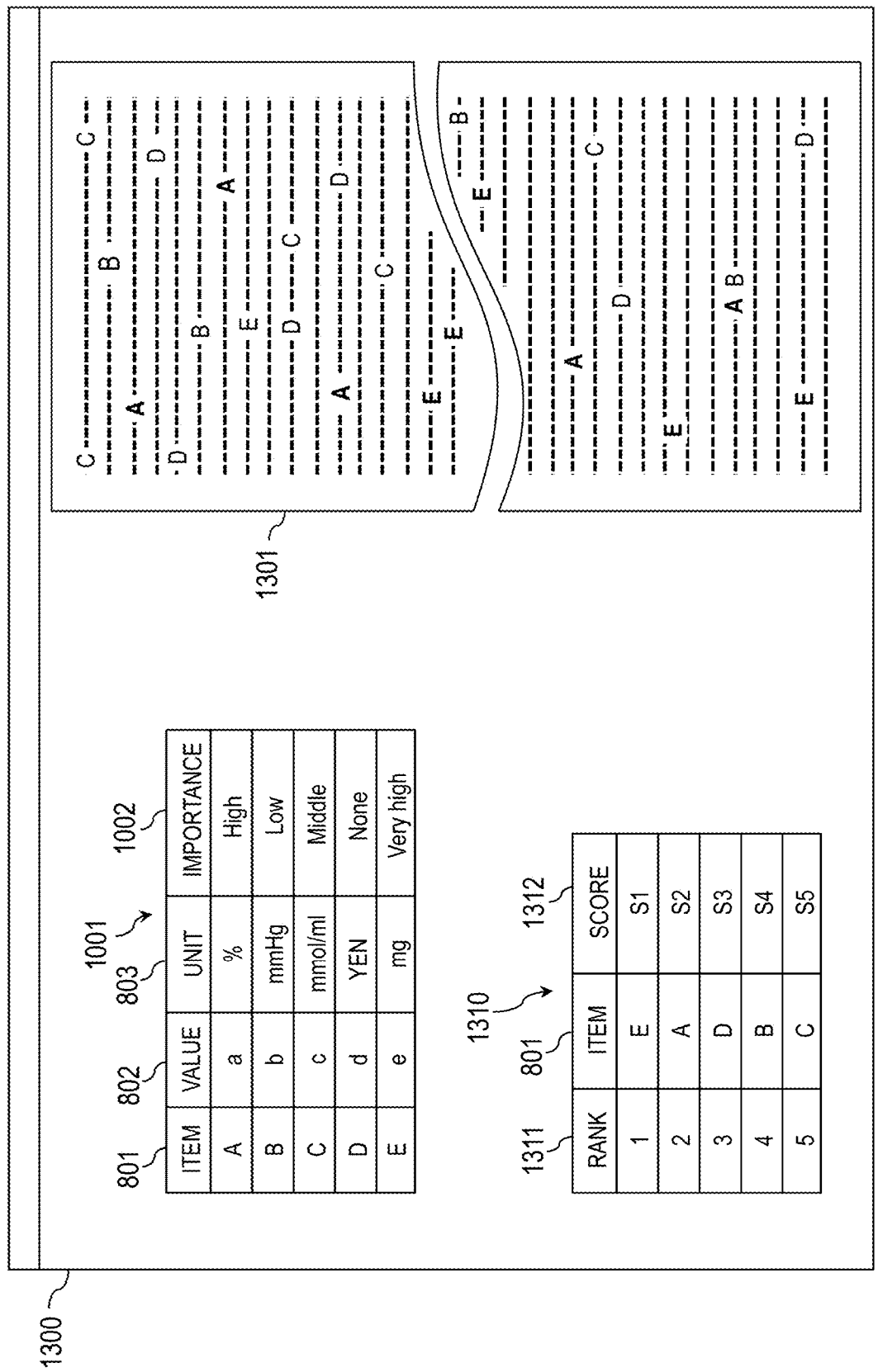
FIG. 13 is an explanatory diagram for illustrating a screen example (Case 4) for displaying the explanation-provided clinical pathway.

FIG. 13 is an explanatory diagram for illustrating a screen example (Case 4) for displaying the explanation-provided clinical pathway CPe. Case 4 is a case in which the clinical pathway CP is an electronic document 1301 including no graphic data, and character strings relating to the item of an important feature are described in the relevant electronic document. The important feature refers to character strings relating to the item whose importance is equal to or larger than "High". A screen of Case 4 is referred to as "fourth screen 1300".

In Case 4, in selection of the clinical pathway CP, the pathway selection module 702 uses, for example, TF-IDF to select the electronic document for which the important feature for the prediction target included in the prediction target model PTM appears most frequently.

On the fourth screen 1300, the importance data 1001, the electronic document 1301, and ranking data 1310 are displayed. The edit module 705 retrieves the relevant character strings (represented by "A" to "E" indicating the items in the electronic document 1301) in the electronic document 1301 so as to be subjected to highlighting processing. In the same manner as in Cases 1 to 3, the edit module 705 creates the importance data 1001. The edit module 705 also assigns weights to the number of items that have appeared with the importance, calculates scores for the respective items, and creates the ranking data 1310 by assigning a rank 1311 to the items in descending order of the score.

In this manner, in the electronic document 1301, it is difficult to identify the diagnosis-and-treatment pathway, and hence the item 801 and a score 1312 are compared with each other instead, to thereby be able to verify to which degree the important feature is included in the electronic document (clinical pathway) 1301. Therefore, when selecting any one of the treatments P2*a* to P2*c* for the relevant patient with the symptom P1, the doctor can provide an explanation by referring to parts in which the items E, A, and C are described as the bases for the selection in the order of the score 1312 of the item 801 in the electronic document 1301.

FIG. 14 is an explanatory diagram for illustrating a screen example (Case 5) for displaying the explanation-provided clinical pathway CPe. Case 5 is a case in which the clinical pathway CP is an electronic document 1301 including no graphic data, and character strings relating to the item of an important feature are not described in the relevant electronic document 1301. A screen of Case 5 is referred to as "fifth screen 1400".

In Case 5, in the same manner as in Case 4, in the selection of the clinical pathway CP, the pathway selection module 702 uses, for example, TF-IDF to select the electronic document for which the important feature for the prediction target included in the prediction target model PTM appears most frequently. On the fifth screen 1400, the importance data 1001 is displayed. The important feature is not described in the electronic document 1301, and hence the electronic document 1301 is not displayed unlike the fourth screen 1300. In the same manner, the ranking data 1310 is not displayed.

In Case 5, the clinical pathway (electronic document 1301) CP is not reliable. Therefore, when selecting a treatment of the prediction target for the relevant patient with the symptom P1, the doctor can provide an explanation by stating the items E, A, and C as the bases for the selection in the order of the importance without using the clinical pathway (electronic document 1301) CP.

(1) As described above, the analysis apparatus 320 includes the explainable vector generation module 704, the neural network NN, the edit module 705, and the output module 706. The explainable vector generation module 704 generates a second piece of input data (explainable vector $z_n$) having weights for first feature items {A to E} based on a first piece of input data (feature vector $x_n$) relating to the first feature items {A to E} of the patient, second feature items {A, C, and E} that define transition criteria (clinical pathway branch criteria CPc) to the prediction targets (P2a to P2c) in the clinical pathway CP relating to a process for the diagnosis or treatment, and the clinical terminology CT indicating the relevance between medical terms.

When being supplied with the first piece of input data (feature vector $x_n$) and the second piece of input data (explainable vector $z_n$) generated by the explainable vector generation module 704, the neural network NN outputs the prediction result 353 for the prediction targets (P2a to P2c) in the clinical pathway CP and importance 1002 of the first feature items {A to E}.

The edit module 705 edits the clinical pathway CP based on the prediction result 353 and the importance 1002, which have been output from the neural network NN. The output module 706 outputs the edit result obtained through the edit performed by the edit module 705.

This allows the interpretability of the relevance between the first feature items {A to E} that have contributed to a prediction based on the machine learning and the clinical pathway CP to be improved with reference to the edit result.

(2) Further, in the analysis apparatus 320 of the above-mentioned item (1), the explainable vector generation module 704 sets the weights for common items {A, C, and E} being the first feature items {A to E} that match the second feature items {A, C, and E} to have values larger than those of the weights for non-common items {B and D} being the first feature items {A to E} that do not match the second feature items {A, C, and E}, to thereby generate the second piece of input data (explainable vector $z_n$).

With this processing, it is possible to assign weights to the feature item with higher weight values as there are more common items, which allows the feature items to be differentiated depending on the importance.

(3) Further, in the above-mentioned item (1), the edit module 705 uses the prediction result 353 and the importance 1002 to generate the explanation information 110 indicating the basis for the prediction result 353, and associates the prediction targets (P2a to P2c) in the clinical pathway CP with the explanation information 110, to thereby generate the explanation-provided clinical pathway CPe as the edit result.

With this processing, it is possible to clarify the relevance between the basis for the explanation of the prediction result 353 and the clinical pathway CP.

(4) Further, in the analysis apparatus 320 of the above-mentioned item (3), the edit module 705 generates the explanation-provided clinical pathway CPe and the importance 1002 of the first feature items {A to E} as the edit result.

With this processing, it is possible to clarify which feature item is important and which feature item is not important, to thereby obtain the basis for the explanation of the prediction result 353.

(5) In the analysis apparatus 320 of the above-mentioned item (3), when the first piece of input data (feature vector $x_n$) satisfies the transition criteria (E≤x and A≥y) for a specific prediction target P2b among the prediction targets (P2a to P2c) and the transition to the specific prediction target P2b is most highly evaluated in the prediction result 353 based on a ranking rule for the prediction targets supplied as the prediction parameter or set as a default value, the edit module 705 generates the explanation information 110 including the suggestion 1013 for recommending the transition to the specific prediction target P2b, and associates the specific prediction target P2b in the clinical pathway CP with the explanation information 110, to thereby generate the explanation-provided clinical pathway CPe as the edit result.

With this processing, the importance of the feature items E, A, and C of the relevant patient become higher in the stated order and the treatment P2b has the highest treatment efficacy probability for the relevant patient in the case of the symptom P1. Therefore, when selecting the treatment P2b for the relevant patient with the symptom P1, the doctor can provide an explanation by stating the items E, A, and C as the bases for the selection in the order of the importance.

(6) In the analysis apparatus 320 of the above-mentioned item (3), when the first piece of input data (feature vector $x_n$) satisfies none of the transition criteria (clinical pathway branch criteria CPc) for the prediction targets (P2a to P2c) but the occurrence probability of the transition to the specific prediction target P2c among the prediction targets (P2a to P2c) is the highest in the prediction result 353, the edit module 705 generates the explanation information 110 including the suggestion 1013 for recommending the transition to the specific prediction target P2c, and associates the specific prediction target P2c in the clinical pathway CP with the explanation information 110, to thereby generate the explanation-provided clinical pathway CPe as the edit result.

With this processing, it is possible to point out the difference between the clinical pathway CP and the prediction result 353. Therefore, when selecting the treatment P2c for the relevant patient with the symptom P1, the doctor can provide an explanation by stating the items E, A, and C as the bases for the selection in the order of the importance. In addition, the accumulation of such cases can contribute to, for example, the review of the clinical pathway branch criteria CPc relating to the treatment P2c and the correction of the clinical pathway CP.

(7) Further, in the analysis apparatus 320 of the above-mentioned item (6), the edit module 705 adds the support data 1114 for supporting the suggestion 1013, which indicates that the transition to the specific prediction target P2c is most highly evaluated in the prediction result 353 based on the ranking rule for the prediction targets supplied as the prediction parameter or set as the default value, to the explanation information 110. With this processing, it is possible to present the basis for the recommendation of the transition to the specific prediction target P2c.

(8) Further, in the analysis apparatus 320 of the above-mentioned item (3), when the first piece of input data (feature vector $x_n$) satisfies none of the transition criteria (clinical pathway branch criteria CPc) for the prediction targets (P2a to P2c) but the occurrence probability of the transition LKa to the non-prediction target P2d is the highest in the prediction result 353, the edit module 705 generates the explanation information 110 including the suggestion 1013 for recommending the transition LKa to the non-prediction target P2d, adds the non-prediction target P2d and the transition LKa to the non-prediction target P2d into the clinical pathway CP, and associates the transition LKa with the explanation information 110, to thereby generate the explanation-provided clinical pathway CPe as the edit result.

With this processing, it is possible to verify that the prediction result 353 is not included in the clinical pathway CP, and to identify a new diagnosis-and-treatment pathway that is not included in the clinical pathway CP and new clinical pathway branch criteria CPc therefor. Therefore, when selecting the treatment P2d for the relevant patient with the symptom P1, the doctor can provide an explanation by stating the items E, A, and C as the bases for the selection in the order of the importance.

(9) Further, in the analysis apparatus 320 of the above-mentioned item (8), the edit module 705 adds the support data 1114 for supporting the suggestion 1013, which indicates that the transition LKa to the non-prediction target P2*d* is most highly evaluated in the prediction result 353 based on the ranking rule for the prediction targets supplied as the prediction parameter or set as the default value, to the explanation information 110. With this processing, it is possible to present the basis for the recommendation of the transition LKa to the non-prediction target P2*d*.

(10) Further, in the analysis apparatus 320 of the above-mentioned item (3), when the clinical pathway CP is the electronic document 1301 formed of at least one sentence and the electronic document 1301 includes terms representing the first feature items {A and E} having a specific importance equal to or higher than a predetermined importance (High), the edit module 705 performs setting that allows the terms representing the first feature items {A and E} having the specific importance to be highlighted, based on appearance frequencies of the terms representing the first feature items {A to E} in the electronic document 1301 and the importance 1002 thereof, and calculates the score 1312 indicating the importance of each of the first feature items {A to E}, to thereby generate the explanation-provided clinical pathway CPe as the edit result.

With this processing, it is possible to verify how many terms representing the first feature items {A and E} having the specific importance are included in the electronic document (clinical pathway) 1301. Therefore, when selecting any one of the treatments P2*a* to P2*c* for the relevant patient with the symptom P1, the doctor can provide an explanation by referring to the parts in which the items E, A, and C are described as the bases for the selection in the order of the score 1312 of the item 801 in the electronic document 1301.

(11) Further, in the analysis apparatus 320 of the above-mentioned item (3), when the clinical pathway CP is the electronic document 1301 formed of at least one sentence and the electronic document 1301 includes no terms representing the first feature items {A and E} having the specific importance equal to or higher than the predetermined importance (High), the edit module 705 generates the importance 1002 of the first feature items {A to E} as the edit result.

With this processing, the doctor can provide an explanation by stating the items E, A, and C as the bases for the transitions to the prediction targets (P2*a* to P2*c*) in the order of the importance 1002 without using the clinical pathway (electronic document 1301) CP.

Further, the analysis apparatus 320 includes the conversion module 501, the rearrangement module 502, and the importance calculation module 504. Therefore, the linear prediction model is obtained through the preliminary rearrangement of the feature vectors $x_n$, and hence it is possible to calculate a predicted value highly accurately with light load at the time of learning and at the time of prediction. It is also possible to grasp what kind of feature is included in the feature vector $x_n$ based on the importance in each tier l from the importance calculation module 504. With this processing, the explanation regarding the feature vector $x_n$ supplied to the neural network NN can be facilitated highly accurately and efficiently.

Further, the analysis apparatus 320 includes the prediction data calculation module 503, and hence the explanation regarding the reason that the prediction result 353 has been obtained for the feature vector $x_n$ by the neural network NN can be implemented highly accurately and efficiently.

Further, the analysis apparatus 320 includes the setting module 505 and the unification module 506, to thereby enable the prediction data calculation module 503 to highly accurately calculate the prediction result 353 based on the rearrangement result.

Further, the analysis apparatus 320 includes the dimensionality reduction module 507, to thereby allow data analysis to become more efficient through dimensionality reduction.

Further, the analysis apparatus 320 can construct a highly accurate prediction model through the learning performed by the learning parameters 365.

It should be noted that this invention is not limited to the above-mentioned embodiments, and encompasses various modification examples and the equivalent configurations within the scope of the appended claims without departing from the gist of this invention. For example, the above-mentioned embodiments are described in detail for a better understanding of this invention, and this invention is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

Further, a part or entirety of the respective configurations, functions, processing modules, processing means, and the like that have been described may be implemented by hardware, for example, may be designed as an integrated circuit, or may be implemented by software by a processor interpreting and executing programs for implementing the respective functions.

The information on the programs, tables, files, and the like for implementing the respective functions can be stored in a storage device such as a memory, a hard disk drive, or a solid state drive (SSD) or a recording medium such as an IC card, an SD card, or a DVD.

Further, control lines and information lines that are assumed to be necessary for the sake of description are described, but not all the control lines and information lines that are necessary in terms of implementation are described. It may be considered that almost all the components are connected to one another in actuality.

What is claimed is:

1. An analysis apparatus, comprising:
   a memory device configured to store a program;
   at least one database storing a plurality of prediction target models corresponding to process for diagnosis or treatment, each prediction target model comprising a plurality of prediction targets and transitions from a starting node to each prediction target forming a plurality of clinical pathways relating to a process for diagnosis or treatment, patient data, and clinical terminology indicating relevance between medical terms; and
   at least one processor coupled to the memory device and the at least one database, the processor configured to execute the program to:
      receive a predictive analytics request comprising patient data and a model parameters, the model parameter indicating a prediction target;
      select a prediction target model from the plurality of prediction target models based on the model parameter generate a feature vector based on the received patient data, the feature vector comprising first feature items and corresponding first input data, each first input data relating to a transition between the starting node and a prediction target of the selected prediction target model;

generate an explanation vector comprising the first feature items and weights for each first feature item, generating the explanation vector comprises:
for each first feature item, determine whether the respective first input data from the feature vector satisfies transition criteria for a prediction target of the selected prediction target model and whether the respective first feature item matches a second feature item indicated by the clinical terminology;
set weights for the first feature items based on the determination, wherein weights for first feature items where transition criteria are satisfied are set higher than weights for first features items where the transition criteria are not satisfied;

select neural network, corresponding to the selected prediction target model, from a plurality of neural networks based on the model parameter, the selected neural network configured to calculate and output, when supplied with and using feature vector and the explanation vector, a prediction result for each of the prediction targets in the clinical pathway of the selected prediction target model and importance of each of the first feature items of the feature vector to the prediction result, wherein the prediction result for each prediction target is a probability of the starting node transitioning to each respective prediction target such that the importance of the each of the first feature items of the feature vector indicates which item of the first feature items of the feature vector, which contributes to the prediction result, has a highest probability;

edit the clinical pathway of the selected prediction target model based on the prediction result and the importance, which have been output from the selected neural network; and output an edit result obtained through the edit for generating a visual representation of the edit results including the prediction results and the importance on a display, wherein the processor is further configured to use the prediction result and the importance to generate explanation information indicating a basis for the prediction result, and associate the prediction target in the clinical pathway with the explanation information, to thereby generate an explanation-provided clinical pathway as the edit result, and wherein the processor is further configured to generate, when the first input data satisfies none of transition criteria for the plurality of prediction targets but a transition to a non-prediction target is most highly evaluated in the prediction result based on one of a ranking rule for the plurality of prediction targets supplied as a prediction parameter and a ranking rule for the plurality of prediction targets set as a default value, the explanation information including a suggestion for recommending the transition to the non-prediction target, add the non-prediction target and the transition to the non-prediction target into the clinical pathway, and associate the transition with the explanation information, to thereby generate the explanation-provided clinical pathway as the edit result.

2. The analysis apparatus according to claim 1, wherein the processor is further configured to generate the explanation-provided clinical pathway and the importance of the first feature item as the edit result.

3. The analysis apparatus according to claim 1,
wherein the processor is further configured to generate, when the first input data satisfies transition criteria for a specific prediction target among the plurality of prediction targets and a transition to the specific prediction target is most highly evaluated in the prediction result based on one of the ranking rule for the plurality of prediction targets supplied as the prediction parameter and the ranking rule for the plurality of prediction targets set as the default value, the explanation information including a suggestion for recommending the transition to the specific prediction target, and associate the specific prediction target in the clinical pathway with the explanation information, to thereby generate the explanation-provided clinical pathway as the edit result.

4. The analysis apparatus according to claim 1,
wherein the processor is further configured to generate, when the first input data satisfies none of the transition criteria for the plurality of prediction targets but a transition to a specific prediction target among the plurality of prediction targets is most highly evaluated in the prediction result based on one of the ranking rule for the plurality of prediction targets supplied as the prediction parameter and the ranking rule for the plurality of prediction targets set as the default value, the explanation information including a suggestion for recommending the transition to the specific prediction target, and associate the specific prediction target in the clinical pathway with the explanation information, to thereby generate the explanation-provided clinical pathway as the edit result.

5. The analysis apparatus according to claim 4, wherein the processor is further configured to add support data for supporting the suggestion for recommending the transition to the specific prediction target, which indicates that the transition to the specific prediction target is most highly evaluated in the prediction result based on one of the ranking rule for the plurality of prediction targets supplied as the prediction parameter and the ranking rule for the plurality of prediction targets set as the default value, to the explanation information.

6. The analysis apparatus according to claim 1, wherein the processor is further configured to add support data for supporting the suggestion, which indicates that the transition to the non-prediction target is most highly evaluated in the prediction result based on one of the ranking rule for the plurality of prediction targets supplied as the prediction parameter and the ranking rule for the plurality of prediction targets set as the default value, to the explanation information.

7. The analysis apparatus according to claim 1, wherein the processor is further configured to perform, when the clinical pathway is an electronic document formed of at least one sentence and the electronic document includes a term representing the first feature item having a specific importance equal to or higher than a predetermined importance, setting that allows the term representing the first feature item having the specific importance to be highlighted, and calculate a score indicating importance of the at least one first feature item based on an appearance frequency of the term representing the at least one first feature item in the electronic document and the importance thereof, to thereby generate the explanation-provided clinical pathway as the edit result.

8. The analysis apparatus according to claim 1, wherein the processor is further configured to generate, when the clinical pathway is an electronic document formed of at least one sentence and the electronic document includes no term representing the at least one first feature item having a specific importance equal to or higher than a predetermined importance, the importance of the at least one first feature item as the edit result.

9. An analysis method, comprising executing, by a processor:
   receiving processing of the receiving a predictive analytics request comprising patient data and a model parameter, the model parameter indicating a prediction target;
   first generation processing of generating a feature vector based on the received patient data, the feature vector comprising first feature items and corresponding first input data, each first input data relating to a transition between a starting node and a prediction target, wherein the patient data is stored in at least one database, the at least one database storing a plurality of prediction target models corresponding to processes for diagnosis or treatment, each prediction target model comprising a plurality of prediction targets and transitions from the starting node to each prediction target forming a plurality of clinical pathways relating to a process for diagnosis or treatment and clinical terminology indicating relevance between medical terms;
   second generation processing of generating an explanation vector comprising the first feature items and weights for each first feature item, the second generation processing comprising:
      selecting a prediction target model from the plurality of prediction target models based on the model parameter:
      for each first feature item, determining whether the respective first input data from the feature vector satisfies transition criteria for a prediction target of the prediction target model and whether the respective first feature item matches a second feature item indicated by the clinical terminology;
      setting weights for the first feature items based on the determination, wherein weights for first feature items where transition criteria are satisfied are set higher than weights for first features items where the transition criteria are not satisfied;
   prediction processing of selecting a neural network, corresponding to the selected prediction target model, from a plurality of neural networks based on the model parameter and predicting by the selected neural network configured to calculate and output, when supplied with and using the feature vector and the explanation vector, a prediction result for each of the prediction targets in the clinical pathway of the selected prediction target model and importance of each of the first feature items of the feature vector to the prediction result, wherein the prediction result for each prediction target is a probability of the starting node transitioning to each respective prediction target such that the importance of the each of the first feature items of the feature vector indicates which item of the first feature items of the feature vector, which contributes to the prediction result, has a highest probability;
   edit processing of editing the clinical pathway of the selected prediction target model based on the prediction result and the importance, which have been output from the selected neural network;
   output processing of outputting an edit result obtained through the edit for generating a visual representation of the edit results including the prediction results and the importance on a display,
      wherein the edit processing comprises using the prediction result and the importance to generate explanation information indicating a basis for the prediction result, and associating the prediction target in the clinical pathway with the explanation information, to thereby generate an explanation-provided clinical pathway as the edit result; and
   third generation processing of generating, when the first input data satisfies none of transition criteria for the plurality of prediction targets but a transition to a non-prediction target is most highly evaluated in the prediction result based on one of a ranking rule for the plurality of prediction targets supplied as a prediction parameter and a ranking rule for the plurality of prediction targets set as a default value, the explanation information including a suggestion for recommending the transition to the non-prediction target, add the non-prediction target and the transition to the non-prediction target into the clinical pathway, and associate the transition with the explanation information, to thereby generate the explanation-provided clinical pathway as the edit result.

* * * * *